United States Patent
Wei et al.

(10) Patent No.: US 11,207,261 B2
(45) Date of Patent: Dec. 28, 2021

(54) PERSONAL CARE COMPOSITIONS WITH TWO BENEFIT PHASES

(71) Applicant: The Procter & Gamble Company, Cincinnati, OH (US)

(72) Inventors: Karl Shiqing Wei, Mason, OH (US); Scott William Syfert, Fort Mitchell, KY (US); Shannon Dale Wagers, Liberty Township, OH (US); Brent William Mason, West Chester, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 16/740,573

(22) Filed: Jan. 13, 2020

(65) Prior Publication Data

US 2020/0146967 A1    May 14, 2020

Related U.S. Application Data

(63) Continuation of application No. 14/937,425, filed on Nov. 10, 2015, now abandoned.
(Continued)

(51) Int. Cl.
| | |
|---|---|
| *A61K 8/00* | (2006.01) |
| *A61K 8/81* | (2006.01) |
| *A61Q 19/10* | (2006.01) |
| *A61K 8/31* | (2006.01) |
| *A61K 8/37* | (2006.01) |
| *A61K 8/92* | (2006.01) |
| *A61K 8/90* | (2006.01) |

(Continued)

(52) U.S. Cl.
CPC .............. *A61K 8/8152* (2013.01); *A61K 8/31* (2013.01); *A61K 8/375* (2013.01); *A61K 8/73* (2013.01); *A61K 8/90* (2013.01); *A61K 8/92* (2013.01); *A61K 8/922* (2013.01); *A61Q 19/00* (2013.01); *A61Q 19/10* (2013.01)

(58) Field of Classification Search
CPC ........... A61K 8/8152; A61K 8/31; A61K 8/92
See application file for complete search history.

(56) References Cited

U.S. PATENT DOCUMENTS

| | | |
|---|---|---|
| 2,020,454 A | 11/1935 | Spaulding |
| 2,438,091 A | 3/1948 | Lynch |

(Continued)

FOREIGN PATENT DOCUMENTS

| | | |
|---|---|---|
| CN | 1145026 A | 3/1997 |
| CN | 1153468 A | 7/1997 |

(Continued)

OTHER PUBLICATIONS

"Composition and Applications of Aloe Vera Leaf Gel", Josias H. Hamman, Published Aug. 8, 2008, Molecules 2008, 13, 1599-1616.
(Continued)

*Primary Examiner* — Necholus Ogden, Jr.
(74) *Attorney, Agent, or Firm* — John G. Powell; Carrie A. Schwartz; Angela K. Haughey

(57) ABSTRACT

Methods of enhancing deposition of a high viscosity benefit agent can include manufacturing a personal care composition comprising the high viscosity benefit agent and a low viscosity benefit agent by adding the high viscosity benefit agent and the low viscosity benefit agent separately to a cleansing phase.

2 Claims, 1 Drawing Sheet

Related U.S. Application Data

(60) Provisional application No. 62/077,690, filed on Nov. 10, 2014.

(51) Int. Cl.
*A61K 8/73* (2006.01)
*A61Q 19/00* (2006.01)

(56) References Cited

U.S. PATENT DOCUMENTS

| | | |
|---|---|---|
| 2,528,378 A | 10/1950 | Mccabe, Jr. |
| 2,658,072 A | 11/1953 | Kosmin |
| 2,798,053 A | 7/1957 | Brown |
| 2,986,271 A | 5/1961 | Forrer |
| 3,455,440 A | 7/1969 | West |
| 3,479,429 A | 11/1969 | Morshauser |
| 3,533,955 A | 10/1970 | Pader |
| 3,542,256 A | 11/1970 | Waterman |
| D220,248 S | 3/1971 | Blumenthal |
| 3,618,757 A | 11/1971 | Funkhouser |
| 3,800,898 A | 4/1974 | Griffin |
| 3,850,365 A | 11/1974 | Dietrich |
| 3,852,475 A | 12/1974 | Tarangul |
| 3,899,076 A | 8/1975 | Florian |
| 3,915,921 A | 10/1975 | Schlatzer, Jr. |
| 3,926,861 A | 12/1975 | Gerecht |
| 3,929,678 A | 12/1975 | Laughlin et al. |
| 3,937,811 A | 2/1976 | Papantoniou |
| 3,940,351 A | 2/1976 | Schlatzer, Jr. |
| 3,951,679 A | 4/1976 | Bernhard |
| 3,980,767 A | 9/1976 | Chown |
| 4,062,817 A | 12/1977 | Westerman |
| 4,159,028 A | 6/1979 | Barker |
| 4,263,363 A | 4/1981 | Buck |
| 4,335,103 A | 6/1982 | Barker |
| 4,379,753 A | 4/1983 | Bolich, Jr. |
| 4,384,096 A | 5/1983 | Sonnabend |
| 4,421,902 A | 12/1983 | Chang |
| 4,425,322 A | 1/1984 | Harvey |
| 4,429,097 A | 1/1984 | Chang |
| 4,514,552 A | 4/1985 | Shay |
| 4,518,578 A | 5/1985 | Hayes |
| 4,600,761 A | 7/1986 | Ruffner |
| 4,616,074 A | 10/1986 | Ruffner |
| D292,879 S | 11/1987 | Smith |
| 4,743,698 A | 5/1988 | Ruffner |
| 4,772,427 A | 9/1988 | Dawson |
| 4,814,160 A | 3/1989 | Carter |
| 4,879,114 A | 11/1989 | Catsimpoolas |
| 4,966,205 A | 10/1990 | Tanaka |
| 4,980,155 A | 12/1990 | Shah |
| 5,002,680 A | 3/1991 | Schmidt |
| 5,011,681 A | 4/1991 | Ciotti |
| 5,059,414 A | 10/1991 | Dallal |
| 5,104,646 A | 4/1992 | Bolich, Jr. |
| 5,106,609 A | 4/1992 | Bolich, Jr. |
| 5,135,748 A | 8/1992 | Ziegler |
| 5,147,576 A | 9/1992 | Montague |
| 5,223,315 A | 6/1993 | Katsura |
| 5,228,912 A | 7/1993 | Herget |
| 5,292,843 A | 3/1994 | Jenkins |
| 5,294,692 A | 3/1994 | Barron |
| 5,304,334 A | 4/1994 | Lahanas |
| 5,342,883 A | 8/1994 | Jenkins |
| 5,364,617 A | 11/1994 | Bush |
| 5,393,450 A | 2/1995 | Shana |
| 5,412,142 A | 5/1995 | Wilkerson, III |
| 5,455,035 A | 10/1995 | Guerrero |
| 5,462,963 A | 10/1995 | Bush |
| 5,487,168 A | 1/1996 | Geiner |
| 5,487,884 A | 1/1996 | Bissett |
| 5,523,619 A | 6/1996 | Mcallister |
| 5,540,853 A | 7/1996 | Trinh |
| 5,556,628 A | 9/1996 | Derian |
| 5,578,299 A | 11/1996 | Starch |
| 5,612,307 A | 3/1997 | Chambers |
| 5,632,420 A | 5/1997 | Lohrman |
| 5,635,171 A | 6/1997 | Nadaud |
| 5,652,228 A | 7/1997 | Bissett |
| 5,661,189 A | 8/1997 | Grieveson |
| 5,681,852 A | 10/1997 | Bissett |
| 5,687,779 A | 11/1997 | Andersson |
| 5,716,920 A | 2/1998 | Glenn, Jr. |
| 5,770,760 A | 6/1998 | Robinson |
| 5,816,451 A | 10/1998 | Renault |
| 5,851,978 A | 12/1998 | Shana |
| 5,873,494 A | 2/1999 | Dallas, Jr. |
| 5,874,495 A | 2/1999 | Robinson |
| 5,914,117 A | 6/1999 | Lavaud |
| 5,916,575 A | 6/1999 | Mcatee |
| 5,925,603 A | 7/1999 | Angelo |
| 5,929,019 A | 7/1999 | Puvvada |
| 5,947,335 A | 9/1999 | Milio |
| 5,952,286 A | 9/1999 | Puvvada |
| 5,954,213 A | 9/1999 | Gerhart |
| 5,965,500 A | 10/1999 | Puvvada |
| 5,965,501 A | 10/1999 | Rattinger |
| 5,965,502 A | 10/1999 | Balzer |
| 5,972,361 A | 10/1999 | Fowler |
| 6,051,386 A | 4/2000 | Lerner |
| 6,068,834 A | 5/2000 | Kvalnes |
| D426,158 S | 6/2000 | Underwood |
| 6,150,312 A | 11/2000 | Puvvada |
| 6,150,313 A | 11/2000 | Harmalker et al. |
| 6,165,395 A | 12/2000 | Kieras |
| 6,174,845 B1 | 1/2001 | Rattinger |
| 6,176,391 B1 | 1/2001 | Rehkemper |
| 6,190,648 B1 | 2/2001 | Kouzu |
| 6,194,364 B1 | 2/2001 | Glenn, Jr. |
| D438,460 S | 3/2001 | Hammond |
| D439,165 S | 3/2001 | Erckelbout |
| 6,213,166 B1 | 4/2001 | Thibiant |
| 6,217,888 B1 | 4/2001 | Oblong |
| D441,645 S | 5/2001 | Longhurst |
| 6,232,496 B1 | 5/2001 | Carr |
| 6,245,323 B1 | 6/2001 | Christie |
| 6,245,344 B1 | 6/2001 | Thibiant |
| 6,268,322 B1 | 7/2001 | St. Lewis |
| D446,121 S | 8/2001 | Maddy |
| 6,270,446 B1 | 8/2001 | Abelbeck |
| D448,678 S | 10/2001 | Bakic |
| 6,306,806 B1 | 10/2001 | St. Lewis |
| 6,335,312 B1 | 1/2002 | Coffindaffer |
| 6,338,855 B1 | 1/2002 | Albacarys |
| 6,340,723 B1 | 1/2002 | Nitta |
| D455,655 S | 4/2002 | Bunce |
| 6,367,519 B2 | 4/2002 | Thibiant |
| 6,383,999 B1 | 5/2002 | Coyle |
| 6,385,992 B1 | 5/2002 | Flore, Jr. |
| 6,394,323 B2 | 5/2002 | Mcclean |
| 6,395,691 B1 | 5/2002 | Tsaur |
| 6,407,044 B2 | 6/2002 | Dixon |
| 6,413,192 B2 | 7/2002 | Abelbeck |
| 6,419,783 B1 | 7/2002 | Rainey |
| 6,426,326 B1 | 7/2002 | Mitra |
| 6,429,177 B1 | 8/2002 | Williams |
| 6,433,061 B1 | 8/2002 | Marchant |
| D467,807 S | 12/2002 | Bakic |
| 6,495,498 B2 | 12/2002 | Niemiec |
| 6,506,391 B1 | 1/2003 | Biatry |
| 6,516,838 B2 | 2/2003 | Thibiant |
| 6,517,939 B1 | 2/2003 | Moini |
| 6,521,216 B1 | 2/2003 | Glandorf |
| 6,523,457 B1 | 2/2003 | Ancona |
| 6,534,456 B2 | 3/2003 | Hayward |
| 6,534,457 B2 | 3/2003 | Mitra |
| 6,534,458 B1 | 3/2003 | Kakizawa |
| 6,537,527 B1 | 3/2003 | Kvalnes |
| 6,547,063 B1 | 4/2003 | Zaveri |
| 6,555,509 B2 | 4/2003 | Abbas et al. |
| 6,564,978 B1 | 5/2003 | Safian |
| 6,574,985 B2 | 6/2003 | Fiore, Jr. |
| 6,589,509 B2 | 7/2003 | Keller |
| 6,635,702 B1 | 10/2003 | Schmucker-castner |

(56) References Cited

U.S. PATENT DOCUMENTS

| | | |
|---|---|---|
| 6,645,511 B2 | 11/2003 | Aronson |
| 6,652,134 B2 | 11/2003 | Lloyd |
| 6,660,251 B1 | 12/2003 | Buenger et al. |
| 6,663,855 B2 | 12/2003 | Frechet |
| 6,673,371 B2 | 1/2004 | Brown |
| 6,673,755 B2 | 1/2004 | Wei |
| D486,398 S | 2/2004 | Lovell |
| 6,691,394 B1 | 2/2004 | Mcclean |
| 6,695,510 B1 | 2/2004 | Look |
| 6,716,440 B2 | 4/2004 | Aronson |
| 6,723,688 B1 | 4/2004 | Malik |
| 6,727,209 B2 | 4/2004 | Pereira |
| 6,759,376 B2 | 7/2004 | Zhang |
| 6,780,826 B2 | 8/2004 | Zhang |
| 6,849,584 B2 | 2/2005 | Geary |
| D502,400 S | 3/2005 | Cinquino |
| D505,079 S | 5/2005 | Mulder |
| 6,897,253 B2 | 5/2005 | Schmucker-castner |
| 6,919,303 B2 | 7/2005 | Pham |
| 6,924,256 B2 | 8/2005 | Massaro |
| D525,872 S | 8/2006 | Haubert |
| D525,873 S | 8/2006 | Haubert |
| 7,084,104 B2 | 8/2006 | Martin |
| 7,098,180 B2 | 8/2006 | Ganopolsky |
| D527,637 S | 9/2006 | Bakic |
| D528,005 S | 9/2006 | Bakic |
| D529,388 S | 10/2006 | Bakic |
| D529,810 S | 10/2006 | Davies |
| 7,119,059 B2 | 10/2006 | Librizzi |
| D533,784 S | 12/2006 | Bakic |
| 7,143,893 B2 | 12/2006 | Kelly |
| 7,144,542 B2 | 12/2006 | Holzer |
| 7,157,414 B2 | 1/2007 | Librizzi |
| 7,229,486 B2 | 6/2007 | Wiersema |
| 7,229,778 B2 | 6/2007 | Hendrix |
| 7,268,104 B2 | 9/2007 | Krzysik |
| 7,273,837 B2 | 9/2007 | Boutique |
| 7,288,616 B2 | 10/2007 | Tamareselvy |
| 7,354,926 B2 | 4/2008 | Lintner |
| 7,488,707 B2 | 2/2009 | Frantz |
| 7,511,003 B2 | 3/2009 | Focht |
| 7,524,807 B2 | 4/2009 | Clapp |
| 7,527,077 B2 | 5/2009 | Mccall |
| 7,531,497 B2 | 5/2009 | Midha |
| 7,537,819 B2 | 5/2009 | Hendricks |
| D601,425 S | 10/2009 | Miller |
| D601,648 S | 10/2009 | Comello, Jr. |
| D608,648 S | 1/2010 | Rhodes |
| 7,649,047 B2 | 1/2010 | Tamareselvy |
| 7,666,825 B2 | 2/2010 | Wagner |
| 7,737,104 B2 | 6/2010 | Hilliard, Jr. |
| 7,749,951 B2 | 7/2010 | Hilliard, Jr. |
| 7,754,666 B2 | 7/2010 | Waiters |
| 7,754,667 B2 | 7/2010 | Walters |
| 7,761,242 B2 | 7/2010 | Honkonen |
| 7,763,419 B2 | 7/2010 | Hendrix |
| 7,767,389 B2 | 8/2010 | Hendrix |
| 7,771,924 B2 | 8/2010 | Hendrix |
| 7,771,925 B2 | 8/2010 | Hendrix |
| 7,776,346 B2 | 8/2010 | Oconnor |
| 7,803,403 B2 | 9/2010 | Librizzi |
| 7,820,609 B2 | 10/2010 | Soffin |
| 7,906,475 B2 | 3/2011 | Walters |
| 7,954,392 B2 | 6/2011 | Belcher |
| D641,633 S | 7/2011 | Carnduff |
| D644,106 S | 8/2011 | Almstead, Jr. |
| 8,025,902 B2 | 9/2011 | Librizzi |
| D646,170 S | 10/2011 | Carnduff |
| 8,029,772 B2 | 10/2011 | Frantz |
| 8,067,517 B2 | 11/2011 | Yoshinaka |
| 8,093,192 B2 | 1/2012 | Liu |
| 8,105,996 B2 | 1/2012 | Wei |
| 8,124,064 B2 | 2/2012 | Wei |
| 8,124,573 B2 | 2/2012 | Focht |
| 8,147,853 B2 | 4/2012 | Taylor |
| 8,158,566 B2 | 4/2012 | Wei |
| D660,181 S | 5/2012 | Nowacek |
| D660,704 S | 5/2012 | Simmons |
| D660,705 S | 5/2012 | Simmons |
| 8,283,852 B2 | 10/2012 | Lee |
| 8,309,667 B2 | 11/2012 | Yoshinaka |
| D674,282 S | 1/2013 | Baldridge |
| D674,292 S | 1/2013 | Klich |
| 8,394,361 B1 | 3/2013 | Frantz |
| 8,417,474 B2 | 4/2013 | Datta |
| D683,226 S | 5/2013 | Baldridge |
| 8,518,991 B2 | 8/2013 | Gunn |
| 8,772,212 B2 | 7/2014 | Restrepo et al. |
| 8,785,397 B2 | 7/2014 | Bernard |
| 8,795,679 B2 | 8/2014 | Einarsson |
| 8,840,871 B2 | 9/2014 | Wei |
| 9,101,551 B2 | 8/2015 | Stella |
| 9,162,085 B2 | 10/2015 | Dihora et al. |
| 9,186,642 B2 | 11/2015 | Dihora |
| 9,216,143 B2 | 12/2015 | Restrepo et al. |
| 9,352,289 B2 | 5/2016 | Beijne et al. |
| 9,671,410 B2 | 6/2017 | Stella |
| 9,675,530 B2 | 6/2017 | Focht |
| 9,717,674 B1 | 8/2017 | Guskey |
| 9,750,674 B2 | 9/2017 | Wei |
| 9,808,408 B2 | 11/2017 | Stella |
| 9,931,282 B2 | 4/2018 | Restrepo et al. |
| 9,943,468 B2 | 4/2018 | Stevenson |
| 10,085,924 B2 | 10/2018 | Wei |
| 10,588,858 B2 | 3/2020 | Tamarkin |
| 10,942,107 B2 | 3/2021 | Wei et al. |
| 10,966,916 B2 | 4/2021 | Wei |
| 10,987,290 B2 | 4/2021 | Wei et al. |
| 2001/0006088 A1 | 7/2001 | Lyle |
| 2002/0042448 A1 | 4/2002 | Sorrentino |
| 2002/0122772 A1 | 9/2002 | Lukenbach |
| 2002/0182112 A1 | 12/2002 | Thorn |
| 2003/0003069 A1 | 1/2003 | Carson |
| 2003/0083210 A1 | 5/2003 | Goldberg |
| 2003/0147842 A1 | 8/2003 | Restle et al. |
| 2003/0161852 A1 | 8/2003 | Miller |
| 2003/0171230 A1 | 9/2003 | Shana'a et al. |
| 2003/0180246 A1 | 9/2003 | Frantz |
| 2003/0207988 A1 | 11/2003 | Tamareselvy |
| 2003/0232101 A1 | 12/2003 | Travis |
| 2004/0009138 A1 | 1/2004 | Kling |
| 2004/0028932 A1 | 2/2004 | Holzer |
| 2004/0057920 A1 | 3/2004 | Focht |
| 2004/0091445 A1 | 5/2004 | Dykstra |
| 2004/0092415 A1 | 5/2004 | Focht |
| 2004/0092425 A1 | 5/2004 | Boutique |
| 2004/0105827 A1 | 6/2004 | Grimm |
| 2004/0146475 A1 | 7/2004 | Peffly |
| 2004/0158940 A1 | 8/2004 | Wells |
| 2004/0180020 A1 | 9/2004 | Manelski |
| 2004/0219119 A1 | 11/2004 | Wei |
| 2004/0223929 A1 | 11/2004 | Clapp |
| 2004/0223939 A1 | 11/2004 | Clausen |
| 2004/0223991 A1 | 11/2004 | Wei |
| 2004/0223992 A1 | 11/2004 | Clapp |
| 2004/0232023 A1 | 11/2004 | Bansal |
| 2004/0235693 A1 | 11/2004 | Wei |
| 2004/0235702 A1 | 11/2004 | Hawkins |
| 2004/0248748 A1 | 12/2004 | Wei |
| 2004/0248749 A1 | 12/2004 | Mitra |
| 2005/0003975 A1 | 1/2005 | Browne |
| 2005/0019299 A1 | 1/2005 | Librizzi |
| 2005/0020468 A1 | 1/2005 | Frantz |
| 2005/0049172 A1 | 3/2005 | Lukenbach |
| 2005/0063930 A1 | 3/2005 | Carlsson |
| 2005/0070452 A1 | 3/2005 | Librizzi |
| 2005/0075256 A1 | 4/2005 | Librizzi |
| 2005/0100570 A1 | 5/2005 | Wei |
| 2005/0129759 A1 | 6/2005 | Sojka |
| 2005/0139574 A1 | 6/2005 | Simone |
| 2005/0143269 A1 | 6/2005 | Wei |
| 2005/0191709 A1 | 9/2005 | Hendrix |
| 2005/0192187 A1 | 9/2005 | Wagner |
| 2005/0192188 A1 | 9/2005 | Wagner |

(56) References Cited

U.S. PATENT DOCUMENTS

| | | |
|---|---|---|
| 2005/0192189 A1 | 9/2005 | Wagner |
| 2005/0221334 A1 | 10/2005 | Benson |
| 2005/0238680 A1 | 10/2005 | Stella |
| 2005/0249758 A1 | 11/2005 | Di Puccio Pagano |
| 2005/0269372 A1 | 12/2005 | Smith |
| 2005/0276768 A1 | 12/2005 | Wei |
| 2005/0287088 A1 | 12/2005 | Guiramand |
| 2006/0002880 A1 | 1/2006 | Peffly |
| 2006/0008438 A1 | 1/2006 | Velarde |
| 2006/0040834 A1 | 2/2006 | Hilliard, Jr. |
| 2006/0042184 A1 | 3/2006 | Perkins |
| 2006/0079417 A1 | 4/2006 | Wagner |
| 2006/0079419 A1 | 4/2006 | Wagner |
| 2006/0079420 A1 | 4/2006 | Wagner |
| 2006/0079421 A1 | 4/2006 | Wagner |
| 2006/0094628 A1 | 5/2006 | Wei |
| 2006/0094635 A1 | 5/2006 | Pereira |
| 2006/0182699 A1 | 8/2006 | Taylor |
| 2006/0189495 A1 | 8/2006 | Librizzi |
| 2006/0193800 A1 | 8/2006 | Reinhardt et al. |
| 2006/0210505 A1 | 9/2006 | Clapp |
| 2006/0257348 A1 | 11/2006 | Walters et al. |
| 2006/0269501 A1 | 11/2006 | Johnson |
| 2006/0276357 A1 | 12/2006 | Smith, III |
| 2006/0276768 A1 | 12/2006 | Miller |
| 2007/0141001 A1 | 6/2007 | Clapp |
| 2007/0155637 A1 | 7/2007 | Smith, III |
| 2007/0187274 A1 | 8/2007 | Dalea |
| 2007/0196344 A1 | 8/2007 | Osborne |
| 2007/0202488 A1 | 8/2007 | Hendrix |
| 2007/0202489 A1 | 8/2007 | Hendrix |
| 2007/0202490 A1 | 8/2007 | Hendrix |
| 2007/0202491 A1 | 8/2007 | Hendrix |
| 2007/0224154 A1 | 9/2007 | Brumbaugh |
| 2007/0224696 A1 | 9/2007 | Honkonen |
| 2007/0248562 A1 | 10/2007 | Berry |
| 2007/0259796 A1 | 11/2007 | Fevola et al. |
| 2007/0280976 A1 | 12/2007 | Taylor |
| 2007/0286832 A1 | 12/2007 | Clapp |
| 2008/0039353 A1 | 2/2008 | Focht |
| 2008/0045428 A1 | 2/2008 | Focht |
| 2008/0045429 A1 | 2/2008 | Focht |
| 2008/0095733 A1 | 4/2008 | Griffin |
| 2008/0112913 A1 | 5/2008 | Librizzi |
| 2008/0196787 A1 | 8/2008 | Comstock |
| 2008/0233061 A1 | 9/2008 | Gates et al. |
| 2008/0242573 A1 | 10/2008 | Wei |
| 2009/0005449 A1 | 1/2009 | Gunn |
| 2009/0005460 A1 | 1/2009 | Gunn |
| 2009/0028809 A1 | 1/2009 | Cetti |
| 2009/0042765 A1 | 2/2009 | Gizaw |
| 2009/0107062 A1 | 4/2009 | Pedersen |
| 2009/0148392 A1 | 6/2009 | SenGupta |
| 2009/0162443 A1 | 6/2009 | Anthony |
| 2009/0209600 A1 | 8/2009 | Miner |
| 2009/0220443 A1 | 9/2009 | Braksmayer |
| 2009/0227751 A1 | 9/2009 | Yoshinaka |
| 2009/0311348 A1 | 12/2009 | Einarsson |
| 2009/0324521 A1 | 12/2009 | Cetti |
| 2010/0022454 A1 | 1/2010 | Norskov-lauritsen |
| 2010/0022455 A1 | 1/2010 | Chilkoti |
| 2010/0022456 A1 | 1/2010 | Christensen |
| 2010/0022458 A1 | 1/2010 | Kopke |
| 2010/0028376 A1 | 2/2010 | Einarsson |
| 2010/0040074 A1 | 2/2010 | Dropps |
| 2010/0040075 A1 | 2/2010 | Kalhoff |
| 2010/0048706 A1 | 2/2010 | Subramanyam |
| 2010/0105102 A1 | 4/2010 | Hanes |
| 2010/0158830 A1 | 6/2010 | Wei |
| 2010/0184847 A1 | 7/2010 | Shin |
| 2010/0190675 A1 | 7/2010 | Cetti |
| 2010/0209374 A1 | 8/2010 | Wei |
| 2010/0216707 A1 | 8/2010 | Bernard |
| 2010/0317677 A1 | 12/2010 | Hassel |
| 2010/0322878 A1 | 12/2010 | Stella |
| 2011/0033842 A1 | 2/2011 | Moon |
| 2011/0038830 A1 | 2/2011 | Bernard |
| 2011/0045037 A1 | 2/2011 | Tamarkin |
| 2011/0045039 A1 | 2/2011 | Sunkel |
| 2011/0064688 A1 | 3/2011 | Jordan |
| 2011/0071123 A1 | 3/2011 | Schwartz |
| 2011/0089196 A1 | 4/2011 | Cetti |
| 2011/0091439 A1 | 4/2011 | Bernard |
| 2011/0117225 A1 | 5/2011 | Wei |
| 2011/0162668 A1 | 7/2011 | Coffindaffer |
| 2011/0165607 A1 | 7/2011 | Takeda |
| 2011/0245124 A1 | 10/2011 | Tsaur et al. |
| 2011/0245125 A1* | 10/2011 | Tsaur .................... A61K 8/737 510/127 |
| 2011/0247954 A1 | 10/2011 | Wei |
| 2011/0250141 A1 | 10/2011 | Wei |
| 2011/0251872 A1 | 10/2011 | Wei |
| 2011/0253157 A1 | 10/2011 | Wei |
| 2011/0253158 A1 | 10/2011 | Wei |
| 2011/0257020 A1 | 10/2011 | Stella |
| 2011/0257030 A1 | 10/2011 | Stella |
| 2011/0257071 A1 | 10/2011 | Miralles |
| 2011/0262025 A1 | 10/2011 | Jarrold |
| 2011/0262570 A1 | 10/2011 | Finlay |
| 2011/0268802 A1 | 11/2011 | Dihora et al. |
| 2011/0269657 A1 | 11/2011 | Dihora |
| 2011/0280822 A1 | 11/2011 | Griffin |
| 2011/0281256 A1 | 11/2011 | Davis |
| 2011/0281366 A1 | 11/2011 | Davis |
| 2011/0305653 A1 | 12/2011 | Jordan |
| 2012/0009285 A1* | 1/2012 | Wei ....................... A61K 8/447 424/757 |
| 2012/0010303 A1 | 1/2012 | Mujkic |
| 2012/0035557 A1 | 2/2012 | Coffindaffer |
| 2012/0087882 A1 | 4/2012 | Fevola |
| 2012/0093753 A1 | 4/2012 | Fevola |
| 2012/0128964 A1 | 5/2012 | Hulse et al. |
| 2012/0184448 A1 | 7/2012 | Stella |
| 2012/0197016 A1 | 8/2012 | Laughlin, II |
| 2012/0258074 A1 | 10/2012 | Mills |
| 2012/0258126 A1 | 10/2012 | Schoeller |
| 2012/0276175 A1 | 11/2012 | Dihora et al. |
| 2012/0276177 A1* | 11/2012 | Hilliard, Jr. ............ A61Q 19/10 424/401 |
| 2012/0276210 A1 | 11/2012 | Dihora |
| 2012/0282309 A1 | 11/2012 | Dihora |
| 2012/0283112 A1 | 11/2012 | Binder |
| 2012/0316095 A1 | 12/2012 | Wei |
| 2013/0115610 A1 | 5/2013 | Lanzalaco |
| 2013/0115648 A1 | 5/2013 | Lanzalaco |
| 2013/0149273 A1 | 6/2013 | Wei |
| 2013/0183360 A1 | 7/2013 | Lips et al. |
| 2013/0225468 A1 | 8/2013 | Corominas |
| 2013/0253057 A1 | 9/2013 | Wei |
| 2013/0280174 A1 | 10/2013 | Lipic |
| 2013/0280192 A1 | 10/2013 | Carter et al. |
| 2013/0280193 A1 | 10/2013 | Carter |
| 2013/0280202 A1 | 10/2013 | Stella |
| 2013/0280356 A1 | 10/2013 | Stella |
| 2013/0281551 A1 | 10/2013 | Stella et al. |
| 2013/0344012 A1 | 12/2013 | Cohen |
| 2014/0023606 A1 | 1/2014 | Scheunemann |
| 2014/0057997 A1 | 2/2014 | Chevalier |
| 2014/0072533 A1 | 3/2014 | Lanzalaco |
| 2014/0131395 A1 | 5/2014 | Chang |
| 2014/0197309 A1 | 7/2014 | Davis |
| 2014/0219946 A1 | 8/2014 | Hloucha |
| 2014/0273055 A1 | 9/2014 | Kerr et al. |
| 2014/0357714 A1 | 12/2014 | Braksmayer |
| 2015/0071977 A1 | 3/2015 | Dihora |
| 2015/0096582 A1 | 4/2015 | Stella |
| 2015/0098920 A1 | 4/2015 | Stella |
| 2016/0122806 A1 | 5/2016 | Amini |
| 2016/0128913 A1 | 5/2016 | Wei |
| 2016/0128927 A1 | 5/2016 | Wei |
| 2016/0128930 A1 | 5/2016 | Stella |
| 2016/0129917 A1 | 5/2016 | Gariepy |
| 2016/0310375 A1 | 10/2016 | Torres Rivera |
| 2017/0000711 A1 | 1/2017 | Jansen |

(56) References Cited

U.S. PATENT DOCUMENTS

| | | |
|---|---|---|
| 2017/0049673 A1 | 2/2017 | Wei |
| 2017/0165155 A1 | 6/2017 | Glenn, Jr. |
| 2017/0165164 A1 | 6/2017 | Zhao |
| 2017/0174413 A1 | 6/2017 | Callens et al. |
| 2017/0228514 A1 | 8/2017 | Apte |
| 2017/0333315 A1 | 11/2017 | Wei |
| 2018/0055894 A1 | 3/2018 | Kim |
| 2018/0110704 A1 | 4/2018 | Zhao |
| 2018/0185255 A1 | 7/2018 | Wei |
| 2018/0353394 A1 | 12/2018 | Skubsch |
| 2018/0360706 A1 | 12/2018 | Dihora |
| 2019/0117546 A1 | 4/2019 | Wei |
| 2019/0142714 A1 | 5/2019 | Dihora |
| 2020/0040373 A1 | 2/2020 | Wei |
| 2020/0172876 A1 | 6/2020 | Wei et al. |
| 2020/0360251 A1 | 11/2020 | Wei |
| 2021/0077372 A1 | 3/2021 | Wei et al. |

FOREIGN PATENT DOCUMENTS

| | | |
|---|---|---|
| CN | 1181006 A | 5/1998 |
| CN | 1248910 A | 3/2000 |
| CN | 1280488 A | 1/2001 |
| CN | 1298293 A | 6/2001 |
| CN | 103813780 A | 5/2014 |
| CN | 110804666 A | 2/2020 |
| DE | 20122018 U1 | 12/2003 |
| DE | 102008035172 A1 | 2/2010 |
| EP | 0078138 A2 | 5/1983 |
| EP | 0937495 A2 | 8/1999 |
| EP | 1005849 B1 | 9/2001 |
| EP | 1064918 B1 | 9/2002 |
| EP | 1243321 A1 | 9/2002 |
| EP | 0907345 | 5/2003 |
| EP | 1657159 B1 | 8/2007 |
| EP | 1383542 B1 | 4/2008 |
| EP | 2505180 A1 | 10/2012 |
| FR | 2233036 A1 | 1/1975 |
| FR | 2792728 A1 | 10/2000 |
| FR | 2908784 B1 | 5/2008 |
| FR | 2924613 B1 | 6/2009 |
| FR | 2924614 B1 | 6/2009 |
| FR | 2925314 B1 | 6/2009 |
| FR | 2924947 B1 | 3/2010 |
| GB | 2245585 A1 | 8/1992 |
| GB | 2431345 B | 5/2009 |
| JP | S61155311 A | 7/1986 |
| JP | H0395110 A | 4/1991 |
| JP | H04149112 A | 5/1992 |
| JP | H06262060 A | 9/1994 |
| JP | 8220550 A | 8/1996 |
| JP | 10216106 A | 8/1998 |
| JP | 2000229817 A | 8/2000 |
| JP | 2002128639 A | 5/2002 |
| JP | 2002138010 A | 5/2002 |
| JP | 200908422 A | 4/2009 |
| JP | 2009126791 A | 6/2009 |
| JP | 2010235567 A | 10/2010 |
| JP | 2011178667 A | 9/2011 |
| KR | 1020110068049 A | 6/2011 |
| KR | 1020120009774 A | 2/2012 |
| KR | 20170102857 A | 9/2017 |
| WO | 9212911 A1 | 8/1992 |
| WO | 9401084 A2 | 1/1994 |
| WO | 9410973 A1 | 5/1994 |
| WO | 9534280 A1 | 12/1995 |
| WO | 9602225 A1 | 2/1996 |
| WO | 9629979 A1 | 10/1996 |
| WO | 9717938 A1 | 5/1997 |
| WO | 9821299 A1 | 5/1998 |
| WO | 9827193 A1 | 6/1998 |
| WO | 9938491 A1 | 8/1999 |
| WO | 9946319 A1 | 9/1999 |
| WO | 0030597 A1 | 6/2000 |
| WO | 0066612 A1 | 11/2000 |
| WO | 0067712 A1 | 11/2000 |
| WO | 0075240 A1 | 12/2000 |
| WO | 0101931 A2 | 1/2001 |
| WO | 0155497 A1 | 8/2001 |
| WO | 02100358 A1 | 12/2002 |
| WO | 03105796 A1 | 12/2003 |
| WO | 2007129330 A1 | 11/2007 |
| WO | 2007129331 A2 | 11/2007 |
| WO | 2008074624 A1 | 6/2008 |
| WO | 2008148672 A1 | 12/2008 |
| WO | 2009001260 A2 | 12/2008 |
| WO | 2009077995 A1 | 6/2009 |
| WO | 2009081368 A2 | 7/2009 |
| WO | 2009081374 A2 | 7/2009 |
| WO | 2010079468 A2 | 7/2010 |
| WO | 2011133538 A1 | 10/2011 |
| WO | 2012138710 A2 | 10/2012 |
| WO | 2015044315 A1 | 4/2015 |

OTHER PUBLICATIONS

13613 PCT International Search Report and Written Opinion for PCT/US2015/059924 dated Jan. 6, 2016.
All Office Actions, U.S. Appl. No. 13/865,554.
All Office Actions, U.S. Appl. No. 13/865,588.
All Office Actions, U.S. Appl. No. 14/937,089.
All Office Actions, U.S. Appl. No. 14/937,335.
All Office Actions, U.S. Appl. No. 14/937,425.
All Office Actions, U.S. Appl. No. 15/859,925.
All Office Actions, U.S. Appl. No. 16/055,604.
All Office Actions, U.S. Appl. No. 16/120,681.
All Office Actions, U.S. Appl. No. 16/165,086.
All Office Actions, U.S. Appl. No. 16/165,146.
All Office Actions, U.S. Appl. No. 16/211,531.
All Office Actions, U.S. Appl. No. 16/697,946.
All Office Actions, U.S. Appl. No. 16/943,888.
All Office Actions, U.S. Appl. No. 17/108,560.
Becker et al., Detection of Differentially Regulated Genes in Keratinocytes by cDNA Array Hybridization: Hsp27 and Other Novel Players in Response to Artificial Ultraviolet Radiation, Journal of Investigative Dermatology, vol. 116, No. 6, Jun. 2001, pp. 983-988.
C. Faller et al. "Predictive ability of reconstructed human epidermis equivalents for the assessment of skin irritation of cosmetics", Toxicology In Vitro., vol. 16, No. 5, Feb. 22, 2002, pp. 557-572.
Cheng Cheng Zhou et al. Self-Aggregation,Antibacterial Activity, and Mildness of Cyclodextrin/Cationic Trimeric Surfactant Complexes 11,ACS Applied Materials & Interfaces, vol. 8, No. 45,Nov. 7, 2016 (Nov. 7, 2016), pp. 30811-30823, XP055557529.
Chng et al. Whole metagenome profiling reveals skin microbiome-dependent susceptibility to atopic dermatitis flare. Nature Microbiology 2016, vol. 1, No. 16106, pp. 1-10.
Clariant "Mild Surfactants Clariant Mild Surfactants for Personal Care Applications" Jul. 23, 2015, 39 Pages.
Cocamidopropyl betaine Product Specification, Edition 1, Jun. 2005, p. 1-51.
Conti et al., "Seasonal influences on stratum corneum ceramide 1 fatty acids and the influence of topical essential fatty acids", International Journal of Cosmetic Science 18, 1-12 (1996).
D.J. Burgess, "Practical Analysis of Complex Coacervate Systems", Journal of Colloid and Interface Science, vol. 140, No. 1, Nov. 1990, pp. 227-238.
Erhirhie et al. "Medicinal Values of Citrullus Lanatus (Watermelon): Pharmacological Review". International Journal of Research in Pharmaceutical and Biomedical Sciences 2013, vol. 4, No. 4, pp. 1305-1312 (Year: 2013).
Ertel et al., Leg wash protocol to assess the skin moisturization potential of personal cleansing products, International Journal of Cosmetic Science, vol. 21, No. Dec. 6, 1999, pp. 383-397.
FDA CFR 21 201.57 (Apr. 1, 2008 edition), p. 24-39.
Flores et al. Microbiome of Affected and Unaffected Skin of Patients with Atopic Dermatitis Before and After Emollient Treatment. Journal of Drugs in Dermatology 2014, vol. 13, issue 11, pp. 611-618 (Year: 2014).

(56) References Cited

OTHER PUBLICATIONS

Geert De Lathauwer, CD Proceeding 6th World Surfactant Congress CESIO, Berlin Germany, Jun. 2004 (paper# 154) (Year: 2004), 9 Pages.

Grando et al., Adrenergic and Cholinergic Control in the Biology of Epidermis: Physiological and Clinical Significance, Journal of Investigative Dermatology vol. 126, pp. 1948-1965 (2006).

Grice and Segre. The skin microbiome. Nature Reviews Microbiology 2011, vol. 9, pp. 244-253 (Year: 2011).

Household Products Database, Brand Information, "Olay Daily Renewal Moisturizing Body Wash, Calming," [Online] URL: http://householdproducts.nlm.nih.gov/cgi-bin/household/brands?tbl=brands&id=16003084, accessed Feb. 8, 2006 (2 pages).

J. Caelles et al., "Anionic and Cationic Compounds in Mixed Systems", Cosmetics & Toiletries, vol. 106, Apr. 1991, pp. 49-54.

J. Crank, The Mathematics of Diffusion, 2nd Edition, 1975, p. 63.

Jing, G. et al., "Parallel-META 3: Compreshensive taxonomical and functional analysis platform for efficient comparison of microbial communities", Scientific Reports, 7:40371, DOI: 10.1038/srep40371 (2017), 11 pages.

Joachim W. Fluhrl et al. "Comparative study of five instruments measuring stratum corneum hydration (Corneometer CM 820 and CM 825, Skicon 200, Nova DPM 9003, DermaLab). Part 11. In vivo", Skin Research and Technology, Jan. 1, 1999, pp. 171-178.

Jun. 2009 (Jun. 2009). "Tahitian Escape Exfoliating Body Wash", XPOQ2752393, Database accession No. 1124626, 3 Pages.

Kikuchi et al., "Improvement of Mild Inflammatory Changes of the Facial Skin Induced by Winter Environment with Daily Applications of a Moisturizing Cream. A Half-Side Test of Biophysical Skin Parameters, Cytokine Expression Pattern and the Formation of Cornified Envelope", Dermatology, vol. 207, No. 3, 2003, pp. 269-275.

KOBO Brochure, Treated Pigments, May 2000, 20 Pages.

Kong et al. Performing Skin Microbiome Research: A Method to the Madness, Journal of Investigative Dermatology 2016, vol. 137, pp. 561-568.

Kong, et al., "Temporal shifts in the skin microbiome associated with disease flares and treatment in children with atopic dermatitis", Genome Research, 2012, vol. 22, pp. 850-859.

Marzatico et al., "Evaluation of anti-wrinkle, elasticizing, ridensifying and skin barrier "repairing" efficacy of a cosmetic treatment", Farcoderm Tested Wellness, BIOTIVIA, Jun. 18, 2009, 42 pages.

Meisel et al., "Skin Microbiome Surveys are strongly influenced by experimental design", Journal of Investigative Dermatology 2016, vol. 136, pp. 947-946 (Year: 2016).

Michael Starch et al., "New Cosmetic Ingredients Based on Metathesized Soybean Oil", ip.com Journal, ip.com Inc., West Henrietta, NY, US, Sep. 9, 2010 (Sep. 9, 2010), XP013140234. 11 Pages.

Michael Starch: "New Cosmetic Ingredients Based on Soybean Oil", ip.com journal, ip.com Inc., West Henrietta NY, US, Jun. 15, 2007, pp. 6, 12, 14.

Milton, Section 9.2: Testing Hypotheses on a Proportion, Introduction to Probability and Statistics, Fourth Edition, Sep. 30, 2002, pp. 129-131.

Mintel Database "Extra Mild Moisturising Bar", XP002752390, Database accession No. 2527423, Sep. 2014 (Sep. 2014, 5 Pages.

Mintel Database "Healthy Shower Gel", Mar. 2011 (Mar. 2011), XP002752392. Database accession No. 1513292, 3 Pages.

Mintel Database, "Shampoo", XP002752391, Database accession No. 2242340, Nov. 2013 (Nov. 2013), 2 Pages.

Niemeyer et al. "A systematic literature review of the human skin microbiome as biomarker for dermatological drug development", British Journal of Clinical Pharmacology 2018, vol. 84, pp. 2178-2193.

Product Data Sheet, N000557—Jun. 2009 (Year: 2009), 1 Page.

Raja K Sivamani et al.: "An Epinephrine-Dependent Mechanism for the Control of UV-Induced Pigmentation", Journal of Investigative Dermatology, vol. 129, No. 3, Aug. 21, 2008 (Aug. 21, 2008), pp. 784-787.

Rimpro India, Surfactant, 2011, 2 Pages.

Rogers et al., "Stratum corneum lipids: the effect of ageing and the seasons, Archives of Dermatological Research" (1996), 288 : 765-770.

Russel M. Walters et al., Cleansing Formulations That Respect Skin Barrier Integrity, Adermatology Research and Practice,vol. 2012, Jan. 1, 2012 (Jan. 1, 2012),pp. 1-9, XP055557527.

Sam Osseiran et al. "Characterizing stratum corneum structure, barrier function, and chemical content of human skin with coherent Raman scattering imaging" Biomedical Optics Express, vol. 9. No. 12, Nov. 26, 2018, 19 Pages.

Schallreuter et al., The induction of the α-1 -adrenoreceptor signal transduction system on human melanocytes, Experimental Dermatology 1996; vol. 5, Issue 1, pp. 20-23.

Scott Truong: "Design of a Handheld Skin Moisture Measuring Device for Application towards Eczema" Apr. 3, 2009, https://macsphere.mcmaster.ca/bitstream/11375/14416/1/fulltext.pdf, pp. 8, 9, 17 and 18.

Seite et al., Barrier function and microbiotic dysbiosis in atopic dermatitis, Clinical, Cosmetic and Investigational Dermatology, vol. 8, 2015, pp. 479-483.

Silva et al. Insights into the skin microbiome dynamics of leprosy patients during multi-drug therapy and in healthy individuals from Brazil. Scientific Reports Jun. 8, 2018, 8:8783, pp. 1-10 (Year: 2018).

Sun et al., A Microbiome-Based Index for Assessing Skin Health and Treatment Effects for Atopic Dermatitis in Children, mSystems, vol. 4, Issue 4, e00293-19, Jul./Aug. 2019.

Tate Owen, Roger Pynn, Jennifer S. Martinez, and Alison Butler; Micelle-to-Vesicle Transition of an Iron-Chelating Microbial Surfactant, Marinobactin E; Nov. 12, 2005; Langmuir, 21,26, 12109-12114 (Year: 2005).

Triethanolamine Product Specification, Chemical Book, 2008, pp. 1-3.

Two et al. The Cutaneous Microbiome and Aspects of Skin Antimicrobial Defense System Resist Acute Treatment with Topical Skin Cleansers. Journal of Investigative Dermatology 2016, vol. 136, pp. 1950-1954 (Year: 2016).

Van Oss, C.J., Coacervation, Complex Coacervation and Flocculation, Journal of Dispersion Science, vol. 9, 1989, 14 pages.

Vaughan, C. D., Solubility, Effects in Product, Package, Penetration and Preservation, , Cosmetics and Toiletries, vol. 103, Oct. 1988, 23 Pages.

Voegeli et al., Efficient and simple quantification of stratum corneum proteins on tape strippings by infrared densitometry, Skin Research and Technology 2007; 13; pp. 242-251.

Weber et al. Steroid-Free Over-the-Counter Eczema Skin Care Formulations Reduce Risk of Flare, Prolong Time to Flare, andu Reduce Eczema Symptoms in Pediatric Subjects With Atopic Dermatitis Journal of Drugs in Dermatology, 2015, vol. 14, Issue 5, pp. 478-485.

www.single-cell.cn/skin search results retrieved Oct. 5, 2019), 1 Page.

Xu et al., "Skin benfits of moisturising body wash formulas for children with atopic dermatitis: A randomised controlled clinical study in China" Australasian Journal of Dermatology (2019), 6 Pages.

Yogiraj et al. Garica papaya Linn: An overview. International Journal of Herbal Medicine 2014, vol. 2, No. 5, pp. 01-08 (Year: 2014).

Zeng et al. High-Altitude Living Shapes the Skin Microbiome in Humans and Pigs. Frontiers in Microbiology 2017, vol. 8, article1929, pp. 1-10 (Year: 2017).

"Dove All Day Moisturizing Body Wash" Online URL: http://www.ewg.org/reports/skindeep2/report.php?type=PRODUCT&id=8801874, XP002332778, 6 Pages.

M. Engelke., "Effects of Xerosis and aging on epidermal proliferation and differentiation", Br. J. Dermatology, vol. 137, 1997, pp. 219-225.

"The validity and practicality of sun-reactive skin types I through VI". Arch. Dermatology, 124: pp. 869-871 (1988).

* cited by examiner

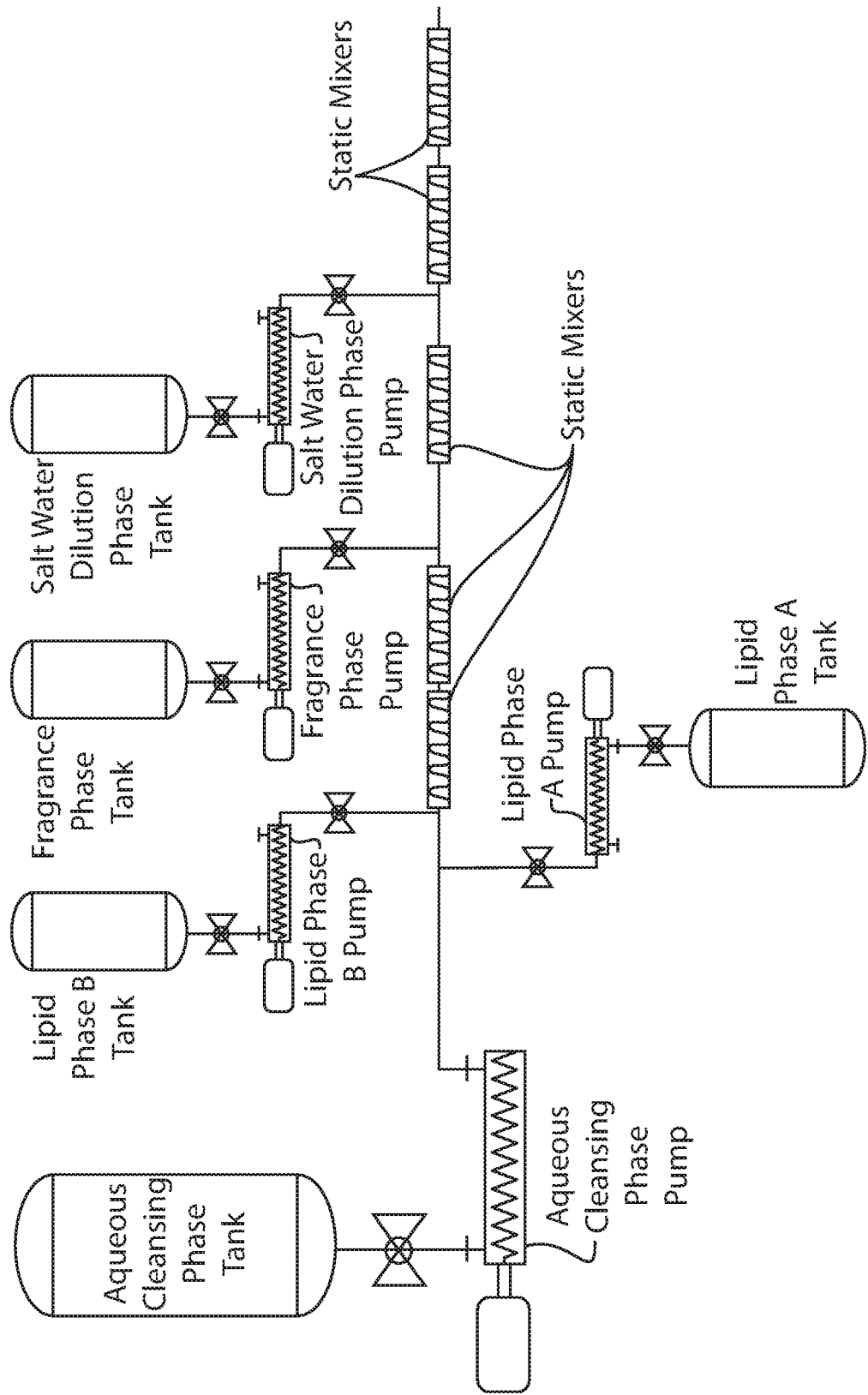

PERSONAL CARE COMPOSITIONS WITH TWO BENEFIT PHASES

TECHNICAL FIELD

The present disclosure generally relates to personal care compositions comprising at least two benefit phases wherein the two or more benefit phases occupy separate physical domains of the personal care composition; and methods relating thereto.

BACKGROUND

Over time, skin cleansing has become part of a personal hygiene regimen. The cleansing of the skin allows for the removal of dirt, debris, bacteria, and a myriad of other things that can cause harm to the skin or the body. Cleansing is often done with the aid of a surfactant. The surfactant works to help remove deposited materials from the skin. Unfortunately, surfactants can also act to remove good things from the skin as well, like lipid. The lipid on the skin helps, for example, to protect the skin from losing too much moisture. Removal of too much lipid can leave the skin vulnerable to becoming dry. One solution for this problem is to utilize a milder surfactant. Another solution is to replace what is removed by depositing a benefit material on the skin. Historically, however, there has been a struggle to effectively deposit these benefit materials on the skin, especially in rinse off products like cleansers. As such, there is a need for personal care compositions that provide enhanced deposition of benefit materials on the skin.

SUMMARY

In one example, a method for enhancing deposition of a high viscosity benefit agent in a personal care composition comprising a cleansing phase; a high viscosity benefit agent; and a low viscosity benefit agent; comprising, adding the high viscosity benefit agent and the low viscosity benefit agent separately to the cleansing phase of the personal care composition.

In another example, a method for enhancing deposition of a high viscosity benefit agent in a personal care composition comprising a high viscosity benefit agent and a low viscosity benefit agent comprising, formulating a personal care composition with a cleansing phase; a first benefit phase having an average particle size of about 50 μm to about 500 μm and comprising a high viscosity benefit agent; and a second benefit phase having an average particle size of about 0.5 μm to about 10 μm and comprising a low viscosity benefit agent.

In another example, a method for enhancing deposition of a high viscosity benefit agent in a personal care composition comprising a cleansing phase, a high viscosity benefit agent, and a low viscosity benefit agent, comprising formulating the personal care composition so that the high viscosity benefit agent and low viscosity benefit agent are in separate physical domains within the personal care composition.

These and other combinations will be better understood from the more detailed description below.

BRIEF DESCRIPTION OF THE DRAWINGS

FIG. 1 is a process diagram for a manufacturing method for multiphase products.

DETAILED DESCRIPTION

While the specification concludes with the claims particularly pointing and distinctly claiming the invention, it is believed that the present invention will be better understood from the following description.

The devices, apparatuses, methods, components, and/or compositions of the present invention can include, consist essentially of, or consist of, the components of the present invention as well as other ingredients described herein. As used herein, "consisting essentially of" means that the devices, apparatuses, methods, components, and/or compositions may include additional ingredients, but only if the additional ingredients do not materially alter the basic and novel characteristics of the claimed devices, apparatuses, methods, components, and/or compositions.

All percentages and ratios used herein are by weight of the total composition and all measurements made are at 25° C., unless otherwise designated.

All measurements used herein are in metric units unless otherwise specified.

I. DEFINITIONS

As used herein, the following terms shall have the meaning specified thereafter:

"Anhydrous" refers to those compositions, and components thereof, which are substantially free of water.

"Associative polymer" refers to a water-dispersible polymer comprising hydrophobic groups at an end or pendants to a hydrophilic backbone.

"High viscosity benefit agent" as used herein refers to a benefit agent with a viscosity of about 1000 cP or more at 25° C. as defined by the viscosity method under the Method Section.

"Low viscosity benefit agent" as used herein refers to a benefit agent with a viscosity of about 500 cP or less at 25° C. as defined by the viscosity method under the Method Section.

"Multiphase" refers to personal care compositions comprising at least two phases of which can be chemically distinct (e.g., a structured cleansing phase and a benefit phase). Such phases can be in direct physical contact with one another. A personal care composition can be a multiphase personal care composition where phases of the personal care composition can be blended or mixed to a significant degree, but still be physically distinct. In these situations, the physical distinctiveness is undetectable to the naked eye. The personal care composition can also be a multiphase personal care composition where phases of the personal care composition can be made to occupy separate and distinct physical spaces inside a package where the phases can be stored. In such an arrangement, the phases can be stored such that they are not in direct contact with one another (i.e., the phases are not separated by a barrier and the phases are not emulsified or mixed to any significant degree). The personal care composition can also be a multiphase personal care composition where the phases are in physical contact and are visually distinct. Visually distinct phases can take many forms (e.g., phases can appear as striped, marbled). The personal care composition can also include a combination of one or more of the above multiphase personal care compositions. In one such arrangement, one blended multiphase personal care composition can be stacked with another blended multiphase personal care composition to form a striped configuration. Additionally, blended multiphase personal care compositions distinguishable by color can be stacked as stripes wherein the blended multiphase personal care compositions can be otherwise similar in average composition.

"Non-associative polymer" refers to a water-dispersible polymer with a relatively uniform hydrophilic backbone lacking hydrophobic groups.

"Package" refers to any suitable container for a personal care composition including but not limited to a bottle, tottle, tube, jar, non-aerosol pump, and combinations thereof.

"Personal care composition" refers to compositions intended for topical application to skin or hair. Personal care compositions can be rinse-off formulations in which the product can be applied topically to the skin and/or hair and subsequently rinsed from the skin and/or hair with water. The product could also be wiped off using a substrate. In either case, it is believed at least a portion of the product is left behind (i.e., deposited) on the skin. The personal care compositions can also be used as shaving aids. The personal care compositions can be extrudable or dispensable from a package. The personal care compositions can exhibit a viscosity from about 1,500 cP to about 1,000,000 cP as measured by a viscosity method as described in the commonly owned patent application published on Nov. 11, 2004 under U.S. Publication No. 2004/0223991 A1 entitled, "Multiphase Personal Care Compositions" filed on May 7, 2004 by Wei, et al. The personal care compositions can be in the form of, for example, a liquid, semi-liquid cream, lotion, or gel and are intended for topical application to the skin and/or hair. Examples of personal care compositions can include but are not limited to shampoo, conditioning shampoo, body wash, moisturizing body wash, shower gels, skin cleansers, cleansing milks, hair and body wash, in shower body moisturizer, pet shampoo, shaving preparations, and cleansing compositions used in conjunction with a disposable cleansing cloth.

"STnS" refers to sodium trideceth(n) sulfate, wherein n can define the average number of moles of ethoxylate per molecule.

"Stable" refers to a personal care composition having a viscosity change of about 30% or less from an initial viscosity value after being rapidly aged for 10 days at 50° C.

"Structured" refers to having a rheology that can confer stability on the personal care composition. A degree of structure can be determined by characteristics determined by the Zero Shear Viscosity Method described below. Accordingly, a structured cleansing phase of the personal care composition can be considered to be structured if the structured cleansing phase has a Zero Shear Viscosity of about 20 Pascal-seconds (Pa-s) or more, about 200 Pa-s or more, about 500 Pa-s or more, about 1,000 Pa-s or more, about 1,500 Pa-s or more, or about 2,000 Pa-s or more. Other methods for determining characteristics which can define a degree of structure are described in U.S. patent application Ser. No. 13/157,665.

The phrase "substantially free of" as used herein, unless otherwise specified, means that the personal care composition comprises less than about 2%, less than about 1%, less than about 0.5%, or even less than about 0.1% of the stated ingredient. The term "free of", as used herein, means that the personal care composition comprises 0% of the stated ingredient that is the ingredient has not been added to the personal care composition. However, these ingredients may incidentally form as a by-product or a reaction product of the other components of the personal care composition.

"Surfactant component" refers to a total of all anionic, nonionic, amphoteric, zwitterionic, and cationic surfactants in a phase. When calculations are based on the surfactant component, water and electrolytes can be excluded from the calculations involving the surfactant component since surfactants as manufactured can be diluted and neutralized.

"Visually distinct" generally refers to a region of the multiphase personal care composition having one average composition, as distinct from another region having a different average composition, wherein the regions can be visible to the unaided naked eye. This would not preclude distinct regions from comprising two similar multiphase personal care compositions or phases where one multiphase personal care composition or phase can comprise certain pigments, dyes, particles, and various optional ingredients, hence providing a region of different average composition (e.g., different textures or different colors).

II. PERSONAL CARE COMPOSITIONS

It can be difficult to both cleanse the skin to remove unwanted things like dirt and deposit beneficial things like benefit agents in the same process. However, this is exactly the goal to be accomplished in a personal care composition with benefit agents. One challenge is to deposit a sufficient amount of skin benefit agents without compromising the cleansing performance such as lather and after-use skin feel. Surfactants commonly used in cleansing compositions tend to diminish the deposition of skin benefit agents. One way to overcome the deposition challenge is through the use of highly viscous hydrophobic material such as petrolatum. But, petrolatum leaves skin greasy/coated which is undesirable for certain consumers. Alternatively, the low viscosity natural triglyceride oil is used in body wash to achieve clean skin feel. But, the low viscosity vegetable oil has poor deposition on skin with less skin benefits. Therefore, it is very difficult to achieve high benefit deposition on skin without compromising performance.

It was previously believed that a low viscosity benefit agent pre-thickened by a group of specific hydrophobic, non-anti-foaming polymers, like petrolatum, provides enhanced deposition of benefit agents in a cleansing composition without compromising lather performance. However, petrolatum is a well-known skin moisturizing agent and blending a low viscosity oil with petrolatum can negatively impact the deposition of petrolatum as skin benefit agent. For example, when petrolatum, a high viscosity benefit agent, is pre-blended with a low viscosity benefit agent, like soy bean oil, the deposition of the petrolatum is sacrificed, having a deposition of about 70 $\mu g/cm^2$. Conversely, if the soy bean oil and petrolatum are added separately to the composition as separate benefit phases, the deposition of the petrolatum is greatly enhanced. A composition made in this fashion deposited from about 270 $\mu g/cm^2$ to about 350 $\mu g/cm^2$.

Without being limited by theory, it is believed that blending low viscosity and high viscosity benefit agents together results in a blended benefit phase with a smaller average particle size of about 10 $\mu m$ or less, where the benefit agents are in a single domain. However, when the two benefit agents are added separately to a cleansing phase, the resulting composition has two different benefit phases with an average particle size of about 50 $\mu m$ or more for the high viscosity benefit phase and an average particle size of about 10 $\mu m$ or less for the low viscosity benefit phase and the two benefit phases occupy separate physical domains. It is believed that the larger particle size benefit agents tend to deposit better because of larger surface area of contact of the benefit agent with the skin surface which increases the adhesion and it becomes harder to remove the lipid particles on the skin with cleansing surfactant. Thus, maintaining the high viscosity benefit agent in separate domain helps to maintain its larger particle size and enhance its deposition.

Thus, a personal care composition with a benefit phase with a particle size of about 50 μm or more are believed to have better deposition onto skin than those benefit phases with smaller particle sizes.

A. Structured Cleansing Phase

As noted herein, a personal care composition can include a structured cleansing phase and a benefit phase. The structured cleansing phase and the benefit phase can be in physical contact. The phases can be blended or mixed to a significant degree, but still be physically distinct such that the physical distinctiveness is undetectable to the naked eye. The phases can also be made to occupy separate and distinct physical spaces inside a package in which the phases can be stored. In such an arrangement, the structured cleansing phase and the benefit phase can be stored such that the phases are not in direct contact with one another. The structured cleaning phase and the benefit phase can be in physical contact while remaining visibly distinct to give, for example, a striped or marbled configuration.

The personal care composition can include a combination of one or more of the above multiphase personal care compositions. For example, one blended multiphase personal care composition can be stacked as stripes with another blended multiphase personal care composition.

The personal care composition can include a cleansing phase. The cleansing phase can comprise as least one anionic surfactant. The cleansing phase may contain from 3% to about 20%, from about 5% to about 15%, from about from about 7% to about 15%, from about 5% to about 13%, from about 5% to about 20%, or any combination of the upper, lower, and included limits within the ranges 2% to 30%, of surfactant, by weight of the personal care composition.

The cleansing phase may comprise a structured domain. The structured domain is preferably an opaque structured domain, which is preferably a lamellar phase. The lamellar phase can provide resistance to shear, adequate yield to suspend particles and droplets while providing long term stability because it is thermodynamically stable. The lamellar phase tends to have a viscosity that minimizes the need for viscosity modifiers, but they can be included if desired. The cleaning phase may comprise more than one surfactant.

The anionic surfactants can be either linear or branched. Examples of some suitable linear anionic surfactants include ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, sodium cocoyl isethionate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Examples of some suitable branched anionic surfactants include but are not limited to the following surfactants: sodium trideceth sulfate, sodium tridecyl sulfate, sodium $C_{12-13}$ alkyl sulfate, sodium $C_{12-15}$ alkyl sulfate, sodium $C_{11-15}$ alkyl sulfate, sodium $C_{12-18}$ alkyl sulfate, sodium $C_{10-16}$ alkyl sulfate, sodium $C_{12-13}$ pareth sulfate, sodium $C_{12-13}$ pareth-n sulfate, sodium $C_{12-14}$ pareth-n sulfate, and combinations thereof. Other salts of all the aforementioned surfactants are useful, such as TEA, DEA, ammonia, potassium salts. Useful alkoxylates include the ethylene oxide, propylene oxide and EO/PO mixed alkoxylates. Phosphates, carboxylates and sulfonates prepared from branched alcohols are also useful anionic branched surfactants. Branched surfactants can be derived from synthetic alcohols such as the primary alcohols from the liquid hydrocarbons produced by Fischer-Tropsch condensed syngas, for example Safol™ 23 Alcohol available from Sasol North America, Houston, Tex.; from synthetic alcohols such as Neodol™ 23 Alcohol available from Shell Chemicals, USA; from synthetically made alcohols such as those described in U.S. Pat. No. 6,335,312 issued to Coffindaffer, et al on Jan. 1, 2002. Suitable examples of alcohols are Safol™ 23 and Neodol™ 23. Suitable examples of alkoxylated alcohols are Safol™ 23-3 and Neodol™ 23-3. Sulfates can be prepared by conventional processes to high purity from a sulfur based $SO_3$ air stream process, chlorosulfonic acid process, sulfuric acid process, or Oleum process. Preparation via $SO_3$ air stream in a falling film reactor is a preferred sulfation process.

The anionic surfactant may also be STnS, wherein n can define average moles of ethoxylation. A structured cleansing phase can include from about 5% to about 20%, from about 7% to about 18%, from about 9% to about 16%, from about 11% to about 14%, by weight of the personal care composition, of STnS. A structured cleansing phase can include from 5% to 20%, from 7% to 18%, from 9% to 16%, from 11% to 14%, by weight of the personal care composition, of STnS. n can range from about 0 to about 3, from about 0.5 to about 2.7, from about 1.1 to about 2.5, from about 1.8 to about 2.2, or n can be about 2. When n is less than 3, STnS can provide improved stability, improved compatibility of benefit agents within the personal care compositions, and increased mildness of the personal care composition. Such described benefits of STnS are disclosed in U.S. patent application Ser. No. 13/157,665.

Further, the structured cleansing phase can comprise a structuring system wherein the structuring system can comprise an associative polymer and a non-associative polymer. The structuring system can comprise from about 0.01% to about 5%, from about 0.05% to about 1%, from about 0.07% to about 0.5%, or from about 0.1% to about 0.3%, by weight of the personal care composition, of a non-associative polymer. The structuring system can also comprise from 0.01% to 5%, from 0.05% to 1%, from 0.07% to 0.5%, or from 0.1% to 0.3%, by weight of the personal care composition, of a non-associative polymer. The structuring system can comprise from about 0.001% to about 5%, from about 0.005% to about 0.5%, from about 0.007% to about 0.05%, from about 0.008% to about 0.04%, or from about 0.01% to about 0.03%, by weight of the personal care composition, of an associative polymer. The structuring system can comprise from 0.001% to 5%, from 0.005% to 0.5%, from 0.007% to 0.05%, from 0.008% to 0.04%, or from 0.01% to 0.03%, by weight of the personal care composition, of an associative polymer.

Such associative polymers can be crosslinked, alkali swellable, associative polymers comprising acidic monomers and associative monomers with hydrophobic end groups, whereby the associative polymer comprises a percentage hydrophobic modification and a hydrophobic side chain comprising alkyl functional groups. Without intending to be limited by theory, it is believed the acidic monomers can contribute to an ability of the associative polymer to swell in water upon neutralization of acidic groups; and associative monomers anchor the associative polymer into structured surfactant hydrophobic domains, e.g., lamellae, to confer structure to the surfactant phase and keep the associative polymer from collapsing and losing effectiveness in the presence of an electrolyte. The crosslinked, associative polymer can comprise a percentage hydrophobic modification, which is a mole percentage of monomers expressed as a percentage of a total number of all monomers in a polymer backbone, including both acidic and other non-acidic monomers. Percentage hydrophobic modification of the associative polymer, hereafter % HM, can be determined by the ratio of monomers added during synthesis or by analytical techniques such as proton nuclear magnetic resonance (NMR). Associative alkyl side chains can comprise, for example, butyl, propyl, stearyl, steareth, cetyl, lauryl, laureth, octyl, behenyl, beheneth, steareth, or other linear, branched, saturated, or unsaturated alkyl or alketh hydrocarbon side chains.

It has also been discovered that crosslinked, associative polymers having certain % HM and certain carbon numbers of hydrophobic end groups of alkyl side chains can provide significant enhancement of structure to personal care compositions comprising a structured surfactant, especially to personal care compositions comprising reduced levels of surfactant. Such associative polymers can also provide the above structure at surprisingly low levels of polymer structurant. Concentrations of associative polymers of up to about 5% or even 10% have been known to provide a sufficient amount structure (e.g., exemplary compositions of U.S. Pat. No. 7,119,059 (Librizzi, et al.) and U.S. Pat. No. 6,897,253 (Schmucker-Castner, et al.). It has been discovered that when an associative polymer % HM and an alkyl side chain number of carbons can be optimized, the structure of an aqueous structured surfactant phase can be increased using only less than about 3 wt %, less than about 2%, less than about 1%, and less than about 0.2%, of an associative polymer, as a percentage of an aqueous structured surfactant phase.

The acidic monomer can comprise any acid functional group, for example sulfate, sulfonate, carboxylate, phosphonate, or phosphate or mixtures of acid groups. The acidic monomer can comprise, for example, a carboxylate. Alternatively, the acidic monomer can be an acrylate, including acrylic acid and/or methacrylic acid. The acidic monomer can comprise a polymerizable structure, e.g., vinyl functionality. Mixtures of acidic monomers, for example acrylic acid and methacrylic acid monomer mixtures, may be useful as well.

The associative monomer can comprise a hydrophobic end group and a polymerizable component, e.g., vinyl, which can be attached. The hydrophobic end group can be attached to the polymerizable component, hence to the polymer chain, by different means but can be attached by an ether or ester or amide functionality, such as an alkyl acrylate or a vinyl alkanoate monomer. The hydrophobic end group can also be separated from the chain, for example, by an alkoxy ligand such as an alkyl ether. The associative monomer can be, for example, an alkyl ester, an alkyl (meth)acrylate, where (meth)acrylate is understood to mean either methyl acrylate or acrylate, or mixtures of the two.

Sometimes, the hydrophobic end group of the associative polymer can be incompatible with the aqueous phase of the personal care composition and can associate with lathering surfactant hydrophobe components. Without intending to be limited by theory, it is believed that longer alkyl chains of structuring polymer hydrophobe end groups can increase incompatibility with the aqueous phase to enhance structure, whereas shorter alkyl chains having carbon numbers closely resembling lathering surfactant hydrophobes (e.g., 12 to 14 carbons) or multiples thereof (for bilayers, e.g.) can also be effective. An ideal range of hydrophobic end group carbon numbers combined with an optimal percentage of hydrophobic monomers expressed as a percentage of the polymer backbone can provide increased structure to the personal care composition comprising a structured surfactant with low levels of polymer structurant.

An exemplary associative polymer can include AQUPEC® SER-300 made by Sumitomo Seika of Japan, which is an acrylate/$C_{10}$-$C_{30}$ alkyl acrylate cross-polymer and comprises stearyl side chains with less than about 1% HM. Associative polymers can comprise about $C_{16}$ (cetyl) alkyl hydrophobic side chains with about 0.7% hydrophobic modification, but a percentage hydrophobic modification can be up to an aqueous solubility limit in surfactant compositions (e.g., up to 2%, 5%, or 10%). Other associative polymers can include stearyl, octyl, decyl and lauryl side chains, alkyl acrylate polymers, polyacrylates, hydrophobically-modified polysaccharides, hydrophobically-modified urethanes, AQUPEC® SER-150 (acrylate/$C_{10}$-$C_{30}$ alkyl acrylate cross-polymer) comprising about $C_{18}$ (stearyl) side chains and about 0.4% HM, and AQUPEC® HV-701EDR which comprises about $C_8$ (octyl) side chains and about 3.5% HM, and mixtures thereof. Another exemplary associative polymer can be Stabylen 30 manufactured by 3V Sigma S.p.A., which has branched isodecanoate hydrophobic associative side chains.

As set forth above, the structured cleansing phase of a personal care composition can further include a non-associative polymer. Suitable non-associative polymers can include water-dispersible polymers with relatively uniform hydrophilic backbone lacking hydrophobic groups. Examples of non-associative polymers can include biopolymer polysaccharides (e.g., xanthan gum, gellan gum), cellulosic polysaccharides (e.g., carboxymethyl cellulose, carboxymethyl hydroxyethyl cellulose), other polysaccharides (e.g., guar gum, hydroxypropyl guar, and sodium alginate), and synthetic hydrocarbon polymers (e.g., polyacrylamide and copolymers, polyethylene oxide, polyacrylic acid copolymers).

Personal care compositions can additionally comprise an organic cationic deposition polymer in one or more phases as a deposition aid for the benefit agents described herein. Suitable cationic deposition polymers can contain cationic nitrogen-containing moieties such as quaternary moieties. Non-limiting examples of cationic deposition polymers can include polysaccharide polymers, such as cationic cellulose derivatives. Cationic cellulose polymers can be salts of hydroxyethyl cellulose reacted with trimethyl ammonium substituted epoxide, referred to in the industry (CTFA) as Polyquaternium 10, which can be available from Amerchol Corp. (Edison, N.J.) in their Polymer KG, JR, and LR series of polymers. Other suitable cationic deposition polymers can include cationic guar gum derivatives, such as guar hydroxypropyltrimonium chloride, specific examples of which can include the Jaguar series commercially available from Rhodia Inc. and N-Hance polymer series commercially available from Aqualon. Deposition polymers can have a cationic charge density from about 0.8 meq/g to about 2.0 meq/g or from about 1.0 meq/g to about 1.5 meq/g, or about 0.96 meq/g.

The personal care composition can be optionally free of or substantially free of sodium lauryl sulfate, hereinafter SLS, and/or ammonium lauryl sulfate, hereinafter ALS, and can comprise at least a 70% lamellar structure. However, in an alternative arrangement, the structured cleansing phase can comprise at least one surfactant, wherein the at least one surfactant includes SLS and/or ALS. Suitable examples of SLS are described in U.S. patent application Ser. No. 12/817,786.

A personal care composition can further comprise from about 0.1% to about 20%, by weight of the personal care composition, of a cosurfactant. The cosurfactant can comprise amphoteric surfactants, zwitterionic surfactants, or mixtures thereof. For example, a personal care composition can include an amphoteric surfactant and/or a zwitterionic surfactant. Suitable amphoteric or zwitterionic surfactants can include those described in U.S. Pat. Nos. 5,104,646 and 5,106,609.

Amphoteric surfactants can include those that can be broadly described as derivatives of aliphatic secondary and tertiary amines in which an aliphatic radical can be a straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoacetate, disodium lauroamphoacetate disodium cocodiamphoacetate, and mixtures thereof. Amphoacetates and diamphoacetates can also be used.

Zwitterionic surfactants suitable for use can include those that are broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocoamidopropyl betaine.

Other suitable surfactants or cosurfactants that can generally be used in a structured cleansing phase for a personal care composition are described in McCutcheon's: Detergents and Emulsifiers North American Edition (Allured Publishing Corporation 1947) (1986), McCutcheon's, Functional Materials North American Edition (Allured Publishing Corporation 1973) (1992) and U.S. Pat. No. 3,929,678 (filed Aug. 1, 1974).

The structured cleansing phase of the personal care composition can also comprise water. The structured cleansing phase of the personal care composition can comprise from about 10% to about 90%, from about 40% to about 85%, or from about 60% to about 80%, by weight of the personal care composition, of water.

Other optional additives can be included in the cleaning phase, including, for example, an emulsifier (e.g., non-ionic emulsifier) and electrolytes. Suitable electrolytes can include anions such as phosphate, chloride, sulfate, citrate, and mixtures thereof and cations such as sodium, ammonium, potassium, magnesium, and mixtures thereof. For example, suitable electrolytes can include sodium chloride, ammonium chloride, sodium sulfate, ammonium sulfate, and mixtures thereof. Other suitable emulsifiers and electrolytes are described in U.S. patent application Ser. No. 13/157,665.

B. Benefit Phase

As noted herein, personal care compositions can include two or more benefit phases. The benefit phases can be hydrophobic and/or anhydrous. The benefit phases can also be substantially free of or free of surfactant.

The First Benefit Phase

The first benefit phase can comprise from about 0.1% to about 20%, by weight of the personal care composition, of a high viscosity skin benefit agent. The first benefit phase comprising a high viscosity benefit agent can have an average particle size of at least about 50 µm, at least about 100 µm, at least 200 µm, at least about 300 µm, to about 10,000 µm.

High viscosity benefit agents can include water insoluble or hydrophobic benefit agents. Examples of high viscosity benefit agents can include petrolatum, microcrystalline wax/mineral oil blends, paraffin wax/mineral oil blend, lanolin, lanolin derivatives, wax/mineral oil blends, triglyceride waxes, synthetic triglycerides, and combinations thereof. Other suitable high viscosity benefit agents are described in U.S. patent application Ser. No. 13/157,665.

High viscosity benefit agents can have a viscosity of about 1,000 cP or more at 25° C. In one example, the viscosity of the high viscosity benefit agent is greater than about 10,000 cP at 25° C. In another example, the high viscosity benefit agent has a viscosity of about 100,000 cP at 25° C. The viscosity of the high viscosity benefit agent can be up to about 1,000,000 cP at 25° C.

The Second Benefit Phase

A personal care composition can comprise a second benefit phase. A second benefit phase can comprise a low viscosity benefit agent. A low viscosity benefit agent has a viscosity of less than about 500 cP at 25° C. In one example, the low viscosity benefit agent has a viscosity of less than 100 cP at 25° C.

An example of a low viscosity benefit agent includes glycerides. Non-limiting examples of low viscosity glycerides suitable for use as low viscosity hydrophobic benefit agents herein can include soybean oil, sun flower seed oil, castor oil, safflower oil, corn oil, walnut oil, peanut oil, olive oil, cod liver oil, almond oil, avocado oil, palm oil, sesame oil, vegetable oils, vegetable oil derivatives, coconut oil and derivatized coconut oil, cottonseed oil and derivatized cottonseed oil, jojoba oil, and combinations thereof.

Another example of a low viscosity benefit agent is SEFOSE® which includes one or more types of sucrose polyesters. Sucrose polyesters are derived from a natural resource and therefore, the use of sucrose polyesters as the benefit agent can result in a positive environmental impact. Sucrose polyesters are polyester materials having multiple substitution positions around the sucrose backbone coupled with the chain length, saturation, and derivation variables of the fatty chains. Such sucrose polyesters can have an esterification ("IBAR") of greater than about 5. For example, the sucrose polyester may have an IBAR of about 5 to about 8. In another example, the sucrose polyester may have an IBAR of about 5-7; in another example, the sucrose polyester can have an IBAR of about 6. In yet another example, the sucrose polyester can have an IBAR of about 8. As sucrose polyesters can be derived from natural resources, a distribution in the IBAR and chain length may exist. For example, a sucrose polyester having an IBAR of 6 may contain a mixture of mostly IBAR of about 6, with some IBAR of about 5, and some IBAR of about 7. Additionally, such sucrose polyesters may have a saturation or iodine value ("IV") of about 3 to about 140. In another example, the sucrose polyester may have an IV of about 10 to about 120.

In yet another example, the sucrose polyester may have an IV of about 20 to 100. Further, such sucrose polyesters may have a chain length of about $C_{12}$ to $C_{20}$.

Non-limiting examples of alkyl esters suitable for use as low viscosity hydrophobic benefit agents herein can include isopropyl esters of fatty acids and long chain esters of long chain (i.e. $C_{10}$-$C_{24}$) fatty acids, e.g., cetyl ricinoleate, non-limiting examples of which can include isopropyl palmitate, isopropyl myristate, cetyl riconoleate, and stearyl riconoleate. Other examples can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of silicone oils suitable for use as low viscosity hydrophobic benefit agents herein can include dimethicone copolyol, dimethylpolysiloxane, diethylpolysiloxane, mixed $C_1$-$C_{30}$ alkyl polysiloxanes, phenyl dimethicone, dimethiconol, and combinations thereof. Non-limiting examples of silicone oils useful herein are described in U.S. Pat. No. 5,011,681. Still other suitable low viscosity hydrophobic skin benefit agents can include milk triglycerides (e.g., hydroxylated milk glyceride) and polyol fatty acid polyesters.

C. Other Optional Materials

Additional optional materials can also be added to the personal care composition to treat the skin, or to modify the aesthetics of the personal care composition as is the case with perfumes, colorants, dyes, or the like. Optional materials useful in products herein can be categorized or described by their cosmetic and/or therapeutic benefit or their postulated mode of action or function. However, it can be understood that actives and other materials useful herein can, in some instances, provide more than one cosmetic and/or therapeutic benefit or function or operate via more than one mode of action. Therefore, classifications herein can be made for convenience and cannot be intended to limit a material to a particularly stated application or applications listed. A precise nature of these optional material and levels of incorporation thereof, will depend on the physical form of the personal care composition and the nature of the cleansing operation for which it is to be used. Optional materials can usually be formulated at about 6% or less, about 5% or less, about 4% or less, about 3% or less, about 2% or less, about 1% or less, about 0.5% or less, about 0.25% or less, about 0.1% or less, about 0.01% or less, or about 0.005% or less by weight of the personal care composition.

The personal care composition can also comprise a benefit component that can be selected from the group consisting of thickening agents; preservatives; antimicrobials; fragrances; chelators (e.g., such as those described in U.S. Pat. No. 5,487,884 issued to Bisset, et al.); sequestrants; vitamins (e.g., Retinol); vitamin derivatives (e.g., tocophenyl actetate, niacinamide, panthenol); sunscreens; desquamation actives (e.g., such as those described in U.S. Pat. Nos. 5,681,852 and 5,652,228 issued to Bisset); anti-wrinkle/anti-atrophy actives (e.g., N-acetyl derivatives, thiols, hydroxyl acids, phenol); anti-oxidants (e.g., ascorbic acid derivatives, tocophenol) skin soothing agents/skin healing agents (e.g., panthenoic acid derivatives, aloe vera, allantoin); skin lightening agents (e.g., kojic acid, arbutin, ascorbic acid derivatives) skin tanning agents (e.g., dihydroxyacteone); anti-acne medicaments; essential oils; sensates; pigments; colorants; pearlescent agents; interference pigments (e.g., such as those disclosed in U.S. Pat. No. 6,395,691 issued to Liang Sheng Tsaur, U.S. Pat. No. 6,645,511 issued to Aronson, et al., U.S. Pat. No. 6,759,376 issued to Zhang, et al, U.S. Pat. No. 6,780,826 issued to Zhang, et al.) particles (e.g., talc, kolin, mica, smectite clay, cellulose powder, polysiloxane, silicas, carbonates, titanium dioxide, polyethylene beads) hydrophobically modified non-platelet particles (e.g., hydrophobically modified titanium dioxide and other materials described in a commonly owned, patent application published on Aug. 17, 2006 under Publication No. 2006/0182699A, entitled "Personal Care Compositions Containing Hydrophobically Modified Non-platelet particle filed on Feb. 15, 2005 by Taylor, et al.) and mixtures thereof. The personal care compositions can comprise from about 0.1% to about 4%, by weight of the personal care composition, of hydrophobically modified titanium dioxide. Other such suitable examples of such skin actives are described in U.S. patent application Ser. No. 13/157,665.

Other optional materials can be those materials approved for use in cosmetics and that are described in the CTFA Cosmetic Ingredient Handbook, Second Edition, The Cosmetic, Toiletries, and Fragrance Association, Inc. 1988, 1992.

III. METHOD OF MANUFACTURING

The personal care compositions as described herein can be manufactured by a multi-benefit stream method. In this method, the components of the cleansing phase are added in a tank with simple mixing to blend the components together. A benefit phase comprising a high viscosity benefit agent is placed into a separate tank and heated to between 50° C. to 80° C. (or above its melting point, whichever is greater). An additional benefit phase comprising a low viscosity benefit agent is placed into a second tank and heated to 20° C.-60° C. (or above its melting point, whichever is greater). Once the components of the cleansing phase are mixed, one of the benefit phases is added to the cleansing phase by injecting the benefit phase into a mixing device such as a static mixer, rotor-stator device, recirculation loop, or into a mixing zone in a mix tank, with the cleansing phase. The remaining benefit phase is then added to the composition in a fashion similar to that of the first benefit phase. This differs from traditional manufacturing where the benefit agents are combined in a single tank, heated, and added to the surfactant phase by simple mixing. The benefit of adding two lipid streams via two different injection points is the creation of two separate particle size domains.

IV. OTHER METHODS

In addition to the compositions above, inventive methods are also present. In one example, a method for enhancing deposition of a high viscosity benefit agent in a personal care composition comprising a cleansing phase; a high viscosity benefit agent; and a low viscosity benefit agent; comprising, adding the high viscosity benefit agent and the low viscosity benefit agent separately to the cleansing phase of the personal care composition.

In another example, a method for enhancing deposition of a high viscosity benefit agent in a personal care composition comprising a high viscosity benefit agent and a low viscosity benefit agent comprising, formulating a personal care composition with a cleansing phase; a first benefit phase having an average particle size of about 50 µm to about 500 µm and comprising a high viscosity benefit agent; and a second benefit phase having an average particle size of about 0.5 µm to about 10 µm and comprising a low viscosity benefit agent.

In another example, a method for enhancing deposition of a high viscosity benefit agent in a personal care composition comprising a cleansing phase, a high viscosity benefit agent, and a low viscosity benefit agent, comprising formulating the personal care composition so that the high viscosity benefit agent and low viscosity benefit agent are in separate physical domains within the personal care composition.

For simplicity, only a minimal amount of compositional ingredients and variants are discussed here. The above disclosure relating to the compositions and ingredients are equally applicable here as well.

V. Test Methods

A. T-Bar Viscosity Method

The viscosity of a personal care composition can be assessed by the T-Bar Viscosity Method. The apparatus for T-Bar measurements includes a Brookfield DV-II+ Pro Viscometer with Helipath Accessory; a chuck, weight and closer assembly for T-bar attachment; a T-bar Spindle D, a personal computer with Rheocalc software from Brookfield, and a cable connecting a Brookfield Viscometer to a computer. First, weigh 80 grams of a personal care composition in a 4-oz. glass jar. Measure a T-bar viscosity by carefully dropping the T-Bar Spindle to an interior bottom of the glass jar and set the Helipath stand to travel in an upward direction. Open the Rheocalc software and set the following data acquisition parameters: Speed to 5 rpm, Time Wait for Torque to 00:01 (1 second), and Loop Start Count to 100. Start data acquisition and turn on the Helipath stand to travel upward at a speed of 22 mm/minute. The T-Bar viscosity is an average T-Bar viscosity reading between the $10^{th}$ reading and the $90^{th}$ reading (the first ten readings and the last ten readings are not used for the average T-Bar viscosity calculation). The T-Bar viscosity reading is provided in cP. After obtaining the initial viscosity reading, place the personal care composition at 50° C. for 10 days for rapid aging. After finishing the stability testing at 50° C., the sample is equilibrated at 25° C. for 24 hours. Then repeat viscosity measurement to obtain final viscosity. Measure percent change of the initial viscosity from the final viscosity measurement to obtain the percent change in viscosity.

B. Zero Shear Viscosity and Young's Modulus Methods

The Zero Shear Viscosity of a material which is a phase or a component of the personal care composition, can be measured either prior to combining in the personal care composition, after preparing a composition, or first separating a phase or component from a personal care composition by suitable physical separation means, such as centrifugation, pipetting, cutting away mechanically, rinsing, filtering, or other separation means.

A controlled stress rheometer such as a TA Instruments AR2000 Rheometer is used to determine the Zero Shear Viscosity. The determination is performed at 25° C. with a 4 cm diameter parallel plate measuring system and a 1 mm gap. The geometry has a shear stress factor of 79580 m−3 to convert torque obtained to stress. Serrated plates can be used to obtain consistent results when slip occurs.

First, material is positioned on a rheometer base plate; the measurement geometry (upper plate) is moved into position 1.1 mm above the base plate. Excess material at the geometry edge is removed by scraping after locking the geometry. The geometry is then moved to the target 1 mm position above the base plate and a pause of about 2 minutes is allowed to allow loading stresses to relax. This loading procedure ensures no tangential stresses are loaded at the measurement onset which can influence the results obtained. If the material comprises particles discernible to the eye or by feel (e.g., beads) that are larger than about 150 microns in number average diameter, the gap setting between the base plate and upper plate is increased to the smaller of 4 mm or 8-fold the diameter of the $95^{th}$ volume percentile particle diameter. If a phase has any particle larger than 5 mm in any dimension, the particles are removed prior to the measurement.

The measurement is performed by applying a continuous shear stress ramp from 0.1 Pa to 1,000 Pa over a time interval of 4 minutes using a logarithmic progression, i.e., measurement points evenly spaced on a logarithmic scale. Thirty measurement points per decade of stress increase are obtained. If the measurement result is incomplete, for example, if material is observed to flow from the gap, results obtained are evaluated with incomplete data points excluded. If there are insufficient points to obtain an accurate measurement, the measurement is repeated with increased number of sample points.

The Young's Modulus (Pa) is obtained by graphing Stress (Pa) vs. Strain (unitless) and obtaining a slope of a regression line of an initial linear region between Stress vs. Strain, typically occurring in the region below about 4% strain. If the relationship is not linear, the linear regression line slope below 2% strain is taken as the Young's Modulus (Pa), using unitless strain.

The Zero Shear Viscosity is obtained by taking a first median value of viscosity in Pascal-seconds (Pa-s) for viscosity data obtained between and including 0.1 Pa and a point where viscosity begins to steeply decline. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

As set forth above, a structured cleansing phase can be considered to be structured if the structured cleansing phase has a Zero Shear Viscosity of about 200 Pa-s or more, about 500 Pa-s or more, about 1,000 Pa-s or more, about 1,500 Pa-s or more, or about 2,000 Pa-s or more.

C. Benefit Agent Viscosity Method A controlled stress rheometer such as a TA Instruments AR2000 Rheometer is used to determine the Viscosity of benefit agent. The determination is performed at 25° C. with a 4 cm diameter parallel plate measuring system and a 1 mm gap. The geometry has a shear stress factor of 79580 m−3 to convert torque obtained to stress. Serrated plates can be used to obtain consistent results when slip occurs.

First, the benefit material is positioned on a rheometer base plate; the measurement geometry (upper plate) is moved into position 1.1 mm above the base plate. Excess material at the geometry edge is removed by scraping after locking the geometry. The geometry is then moved to the target 1 mm position above the base plate and a pause of about 2 minutes is allowed to allow loading stresses to relax. This loading procedure ensures no tangential stresses are loaded at the measurement onset which can influence the results obtained. If the material comprises particles discernible to the eye or by feel (e.g., beads) that are larger than about 150 microns in number average diameter, the gap setting between the base plate and upper plate is increased to the smaller of 4 mm or 8-fold the diameter of the $95^{th}$ volume percentile particle diameter. If a phase has any particle larger than 5 mm in any dimension, the particles are removed prior to the measurement.

The measurement is performed by applying a continuous shear stress ramp from 0.1 Pa to 1,000 Pa over a time interval of 4 minutes using a logarithmic progression, i.e., measurement points evenly spaced on a logarithmic scale. Thirty measurement points per decade of stress increase are obtained. If the measurement result is incomplete, for example, if material is observed to flow from the gap, results obtained are evaluated with incomplete data points excluded. If there are insufficient points to obtain an accurate measurement, the measurement is repeated with increased number of sample points.

The Viscosity of the benefit agent is obtained by graphing Viscosity (Pa.S) vs. Shear Rate (/s) and obtaining consistency value (K) and shear index (n) through a power law fit. The consistency value (K) is defined as the benefit phase/agent viscosity.

D. Third-Phase Method for Determining Structured Surfactant Stability

A Third-Phase Method can be used to determine structured surfactant phase stability in a personal care composition. The method involves placing the personal care compositions at 50° C. for 10 days for rapid aging. After rapid aging, transfer about 4 grams of the personal care composition into a Beckman Centrifuge Tube (11 mm×60 mm). Place the centrifuge tube in a Beckman LE-80 Ultracentrifuge and operate the ultracentrifuge under the following conditions: 50,000 rpm, 2 hours, and 40° C.

After ultracentrifugation, determine the third-phase volume by measuring a height for each of various surfactant phases using an Electronic Digital Caliper (within 0.01 mm).

A very top layer is a hydrophobic benefit phase layer (e.g., hydrocarbons or soybean oil). The layers below the hydrophobic benefit phase layers containing surfactant/water can determined by the following: Ha is a height of all layers containing surfactant/water and Hb is a height of a clear "third-phase" layer just below the hydrophobic benefit phase layer. It is important to record the readings within 30 minutes after the ultracentrifugation is finished to minimize material migration across different layers. The third phase volume is calculated as: Third-Phase Volume %=Hb/Ha*100%.

A personal care composition comprising a structured surfactant can comprises less than about 10% "third-phase" volume, less than about 5% "third-phase" volume, less than about 2% "third-phase" volume, or less than about 1% "third-phase" volume after rapid aging stability protocol. In another arrangement, the personal care composition comprising a structured surfactant can comprise about 0% "third-phase" volume after rapid aging protocol.

E. Ultracentrifugation Method

The Ultracentrifugation Method is a physical method used to determine an amount of structure in a personal care composition or a subset of a personal care composition. The method can also be used to determine a rate at which a personal care composition comprising a structured surfactant dissolves upon dilution to present effective amounts of surfactant to a cleaning environment proximal to surfaces.

A personal care composition can be separated by ultracentrifuge into separate but distinguishable layers. The personal care composition can have multiple distinguishable layers (e.g., a structured surfactant layer and a benefit layer).

First, dispense about 4 grams of the personal care composition into a Beckman Centrifuge Tube (11 mm×60 mm) to fill the tube. Next, dilute the personal care composition to a 10% Dilution Level using 90% of the personal care composition and 10% DI water using an appropriate mixer and dispense an equal amount of the personal care composition into a companion centrifuge tube. Continue to dilute the personal care composition and fill tubes in the same manner until a 60% Dilution Level is obtained for the personal care composition using 40% of the personal care composition with 60% DI water. Place the centrifuge tubes in an ultracentrifuge (Beckman Model L8-M or equivalent) using a sling rotor and ultracentrifuge using the following conditions: 50,000 rpm, 2 hours, and 40° C.

Measure relative phase volumes for each phase of the personal care composition by measuring a height for each layer using an Electronic Digital Caliper (within 0.01 mm). Layers are identified by those skilled in the art by physical observation techniques paired with chemical identification if needed. For example, the structured surfactant layer can be identified by transmission electron microscopically (TEM), polarized light microscopy, and/or X-ray diffraction as a structured lamellar phase comprising multilamellar vesicles, and the hydrophobic benefit layer can be identified by its low moisture content (less than about 10% water as measured by Karl Fischer Titration). Measure a total height Ha, which includes all materials in the ultracentrifuge tube. Next, the height of each layer is measured from a bottom of the centrifuge tube to a top of the layer, and the span of each layer can be algebraically determined by subtraction. The benefit layer may comprise several layers. If the benefit phase splits, a sum of the benefit layers measured is the benefit layer height, Hb. Generally, a hydrophobic benefit layer, when present, is at a top of the centrifuge tube.

The surfactant phase may comprise several layers or a single layer, Hc. There may also be a micellar, unstructured, clear isotropic layer at the bottom or next to the bottom of the ultracentrifuge tube. Layers immediately above the isotropic phase generally comprise higher surfactant concentration with higher ordered structures (such as liquid crystals). Such structured layers can be opaque to naked eyes, or translucent, or clear. If several structured layers are present, Hc is a sum of individual structured layers. If any type of polymer-surfactant phase is present, it is considered a structured phase and included in the measurement of Hc. A sum of aqueous phases is Hs.

Finally, the structured domain volume ratio is calculated as follows:

Structured Domain Volume Ratio=$Hc/Hs*100\%$

If there is no benefit phase present, use the total height as the surfactant layer height, Hs=Ha. The Structured Domain Volume Ratio is the Lamellar Phase %. The measurement is made for each dilution prepared and centrifuged (i.e., the Structured Domain Volume Ratio is determined for the composition, and for 90%, 80%, 70% and 60% dilutions prepared as indicated above).

The highest amount of dilution (i.e., the lowest Dilution Level) wherein the personal care composition maintains at least 95% Lamellar Phase % is an indicator of amount of structure for personal care compositions having varying n values for STnS.

The highest dilution wherein the personal care composition has at least 95% lamellar phase is greater than about 15%, greater than about 25%, or greater than about 35%.

The personal care composition has a Structured Domain Volume Ratio of greater than about 40%, greater than about 45%, greater than about 50%, greater than about 55%, greater than about 60%, greater than about 65%, greater than about 70%, greater than about 75%, greater than about 80%, greater than about 85%, or greater than about 90%, by volume of personal care composition comprising an aqueous surfactant.

F. Lipid Particle Size Measurement

Lipid particle size is measured in neat product under a differential interference contrast optical microscope with a 10× objective lens. The particle size distribution is counted manually. All lipid particles are assumed as uniform spheres in this application. For irregular shaped lipid particles, the longest axis is used as the diameter for the particle size distribution counting. The number weighted average of all lipid particles is defined as the average lipid particle size.

G. In-vitro Deposition Method

In-vitro Deposition Evaluation Method: The In-vitro Deposition Evaluation Method measures the deposition of benefit agents on a skin mimic. The method compares the quantity of benefit agent of the skin mimic surface before and after cleansing in an automated cleansing unit, such as the automated cleansing unit described in co-pending and co-assigned Multiphase Personal Care Composition With Enhanced Deposition, U.S. application Ser. No. 12/510,880 (filed Jul. 28, 2009) and In-Vitro Deposition Evaluation Method for Identifying Personal Care Compositions Which Provide Improved Deposition of Benefit Agents, U.S. application Ser. No. 12/511,034 (filed Jul. 28, 2009).

The In-vitro Deposition Evaluation Method uses two 12-well plates (hereinafter referred to as "plates"). Suitable 12-well plates are commercially available from Greiner bio-one. For example, the Cellstar® 12 well suspension culture plate has 3 rows and 4 columns with a well volume of about 6.2 mL. The Cellstar® 12 well suspension culture plate comprises the approximate dimensions of 19 mm in height, 127 mm in length and 85 mm in width. The Cellstar® 12 well suspension culture plate has a well diameter of 23 mm, a well depth of 15 and a well to well spacing of 2 mm A Cellstar® 12 well suspension culture plate is provided for containing the samples comprising the personal care composition in the Examples above.

The In-vitro Deposition Evaluation Method uses approximately 120 g of bodies for two plates. Five grams of bodies carefully loaded into each of the 12 wells of the two plates to ensure the same quantity is loaded into each well. Each body is a spherical stainless steel bearing that is approximately 2 mm in circumference. Each body comprises ferrometallic material. Suitable bodies are those available from WLB Antriebeselemente Gmbh, Scarrastrasse 12, D-68307 Mannheim, Germany.

The personal care compositions are prepared according to the description in the Example Section above. After the examples of the personal care compositions are prepared, control and test samples are prepared by determining the dilution ratio and dispensing both the personal care composition and distilled water into the wells of the microplate and allow the samples to mix while being exposed to the automated washing process. The dilution ratio used in this application is one part of composition and twenty nine parts of water (1:29). A pre-calibrated positive displacement pipette is used to dispense 66.7 µL of composition on to the bodies in each well, followed by dispensing 1933.3 µL of distilled water into each well. The control samples and test samples are dispensed in the specified wells of the plate, all within a 20 minute time frame. Each composition is placed in 6 different well, 3 of which are in plate 1 and the other 3 well are in plate 2. A test control composition containing the benefit agent should be used in every test to ensure consistency among tests.

The skin mimic used in the In-vitro Deposition Evaluation Method is comprised of a molded bicomponent polyurethane substrate. The skin mimic is textured on one side with a pattern that resembles the texture of human skin. The textured side of the skin mimic is coated with 1, 1, 1-trimethyl-1-pentene that is plasma deposited. The skin mimic surface has a total surface energy of 32±1.0 (mJ/m$^2$) and a contact angle in water of 100°±2.0. Suitable skin mimic surface materials are described in co-pending and co-assigned Coated Substrate with Properties of Keratinous Tissue, U.S Patent Pub. No. 20070128255A1 (filed Aug. 11, 2006) (published Jun. 7, 2007) and Methods of Use of Substrate Having Properties of Keratinous Tissue, U.S Patent Pub. No. 20070288186A1 (filed Feb. 5, 2007) (published Dec. 13, 2007).

After all of the wells of the plate are filled with the samples and the pieces of skin are made and coated, the skin mimic is prepared for the In-vitro Deposition Evaluation Method. Two pieces of skin mimic are prepared by cutting the skin mimic to fit on top of all 12 openings of the wells of the plate while wearing gloves. The two pieces of skin mimic pieces are numbered "1" and "2".

Next, the pieces of skin mimics are arranged over the openings of the wells of the microplates. The pieces of skin mimic surface material are transferred to cover the openings of the wells of the each of the plates to ensure that the textured and treated region of the skin mimic is facing the openings of the wells of the plate. A lid is placed over each piece of the skin mimic and the associated plate to form a lidded plate.

The lidded plates are placed into plate holders of an automated cleansing unit, or, a device used in the in-vitro Deposition Evaluation Method of the present invention. The automated cleansing unit comprises a horizontal base comprising four microplate holders. The horizontal base is made of rectangle of aluminum comprising the following approximate dimensions of ⅜ inch in height, fourteen inches in width and twenty seven inches in length. The automated cleansing unit further comprises two vertical supports comprised of aluminum with the approximate dimensions of one inch by two inches by ten and ¾ of an inch in height. The vertical supports are attached to a horizontal support comprising a rodless air slide. The horizontal support comprising a rodless air slide comprises the approximately dimension of a ½ inch by two inches by twenty six and ½ inches in height. Suitable rodless air slides comprise a one inch bore and eleven inch stroke and have associated end lugs and mount brackets, which are commercially available from McMaster-Carr. The rodless air slide can be double acting and comprises a carriage that is connected to an internal piston and two compressed air ports.

The automated cleansing unit comprises two magnetic arms. The horizontal support comprising a rodless air slide is the structure upon which the two magnetic arms are mounted. The magnetic arms are mounted to the rodless air slide such that the magnetic arms move back and forth along the length of the double acting rodless air slide by the force of compressed air. Each of the magnetic arms are comprised of aluminum and have the approximate dimensions of one inch by two inches by fourteen inches in length and have a "T" shape channel that houses seven neodymium iron boron magnets (not shown). Each of the neodymium iron boron magnets has the approximate dimensions of two inches in length, one inch in width and half or an inch in height. Each of the neodymium iron boron magnets comprises a magnetic strength of 12200 Gauss, available from Edmund Scientifics.

The magnetic arms are configured at a height of about 2.75 cm above the microplate holder with the caveat that the magnets maintain their function to attract and move the bodies comprised within the wells of the microplate. The magnetic arms move back and forth along the length of the rodless air slide by the force of compressed air at a speed of approximately 6 back and forth sweeps over the length of the rodless air slide over a 10 second time period.

The magnetic arms can be configured with four microplate holders. Each of the microplate holders comprise a clamping plate and four pistons attached to a pneumatic control unit. When actuated, the pistons for the pneumatic control unit hold the plates in the four plate holders at a pressure of about 90 psi. Prior to placing the lidded plates into the plate holders of automated cleansing unit, the pneumatic control unit is turned on.

The automated cleansing unit can comprise a pneumatic control unit. The top view shows components of the pneumatic control unit which can be connected to the rodless air slide, the piston and clamping plates. The pneumatic control unit can be used to apply compressed air to the automated cleansing unit, which imparts a force by converting the potential energy of compressed air into kinetic energy. The pneumatic control unit comprises a solenoid air control valve, a distribution manifold outlet, a compressed air control valve, a compressed air flow regulator, an alternating output binary valve, a two-hand safety pneumatic control valve, a compressed air control valve and various connectors that provide pressurized air to the automated cleansing unit from an external air source. The air control valve, air flow regulators, alternating a binary valves, a two-hand safety pneumatic control valve are positioned upstream of a solenoid air control valve. A suitable solenoid air control valve can be described as a double air style valve with a 10 psi to 120 operating pressure. Suitable compressed air flow regulators can operate, for example, in the pressure range of 14 psi to 116 psi. Suitable air control valve alternating output binary valves 40 can operate, for example, in a 35 psi to 100 psi range. All of the components of the pneumatic control unit are available from McMaster-Carr®.

The lidded plates are placed into the plate holders and pneumatic control unit is actuated such that the lidded plates are held under 90 psi of pressure. The magnetic arms are actuated on and arms moves over the lidded microplates at a height of 2.65 cm above the plate holders. The magnetic arms of the automated cleansing unit, sweep back and forth over the plate holders for 5 minutes, at a speed of 6 sweeps per every 10 seconds. After 5 minutes of the automated cleansing process, the lidded plates are removed from the plate holders and are disassembled.

After the automated washing process, two large 4000 ml beakers of 20° C. to 25° C. water are filled. The first piece of skin mimic is removed from the first plate and submerged in the tap water within the first beaker five times. The second piece of skin mimic is removed from the second microplate and submerged within the second beaker five times. The completeness of rinsing step is judged visually by the lack of foam on the skin mimic and presence of defined circles of deposited material on the skin mimic. Both piece of skin mimic are blotted gently with paper towels and fumed in a drying hood for at least 3 hours each.

The cut-out pieces of treated skin mimic are then extracted with a solvent and the extract is analyzed and quantified by gas chromatography.

V. EXAMPLES

| I: Personal Care Composition | Base formula |
|---|---|
| 1) Aqueous Cleansing Phase | |
| Sodium Trideceth Ether Sulfate | 8.63% |
| Cocamidopropyl Betaine | 2.58% |
| Trideceth-3 | 1.37% |
| Sodium Chloride | 4.45% |
| Guar Hydroxypropyltrimonium Chlroide | 0.45% |
| (N-Hance CG-17 from Aqualon) | |
| Xanthan Gum | 0.03% |
| (Keltrol 1000 from CP Kelco) | |
| Acrylates/C10-30 Alkylacrylate Cross Polymer | 0.03% |
| (Aqupec SER-300C from Sumitomo) | |
| Methyl chloro isothiazolinone and methyl | 0.04% |
| isothiazolinone (Kathon CG, Rohm & Haas) | |
| EDTA (Dissolvine NA 2x) | 0.14% |
| Sodium Benzoate | 0.28% |
| Perfume | 1.25% |
| Citric Acid, titrate | pH = 5.7 ± 0.2 |
| Water and minors | Q.S. |
| 2) Lipid Phase A | |
| RBD Soybean Oil | 2.43% |
| Glyceryl Oleate | 0.025% |
| BHT | 0.05% |
| 3) Lipid Phase B | |
| Petrolatum | 2.50% |

The aqueous surfactant phase can be prepared through conventional mixing technique. The order of addition is as follow in the mixing vessel: water, sodium chloride, sodium trideceth sulfate, cocamidopropyl betaine, trideceth-3, guar hydroxypropyl trimonium chloride, Xanthan gum, Acrylates/C10-C30 Alkylacrylates cross polymer, EDTA, sodium benzoate. Adjust pH to 5.7 with citric acid. Then add Kathon and perfume. Keep mixing until homogenous. A benefit phase comprising a high viscosity benefit agent is placed into a separate tank and heated to between 50° C. to 80° C. (or above its melting point, whichever is greater). An additional benefit phase comprising a low viscosity benefit agent is placed into a second tank and heated to 20° C.-60° C. (or above its melting point, whichever is greater). Once the components of the cleansing phase are mixed, one of the benefit phases is added to the cleansing phase by injecting the benefit phase into a mixing device such as a static mixer, rotor-stator device, recirculation loop, or into a mixing zone in a mix tank, with the cleansing phase. The remaining benefit phase is then added to the composition in a fashion similar to that of the first benefit phase.

A sample process diagram for a manufacturing method is shown in FIG. 1.

The order of addition of the phases and the mixing is changed as noted below for each example.

Changes to this manufacturing method for each example are listed below.

| | Example 1 | Example 2 | Example 3 | Example 4 | Example 5 | Example 6 | Example 7 | Comparative Example A |
|---|---|---|---|---|---|---|---|---|
| II: Personal Care Process Configuration | Aqueous Cleaning Phase Infusion<br>Lipid B Infusion<br>Lipid A Infusion<br>2-6 mm static mixers<br>1-10 mm static mixer<br>Salt Water Dilution Phase Infusion<br>2-10 mm static mixers | Aqueous Cleaning Phase Infusion<br>Lipid A Infusion<br>Lipid B Infusion<br>2-6 mm static mixers<br>1-10 mm static mixer<br>Salt Water Dilution Phase Infusion<br>2-10 mm static mixers | Aqueous Cleaning Phase Infusion<br>Lipid A Infusion<br>2-6 mm static mixers<br>Lipid B Infusion<br>2-6 mm static mixers<br>1-10 mm static mixer<br>Salt Water Dilution Phase Infusion<br>2-10 mm static mixers | Aqueous Cleaning Phase Infusion<br>Lipid B Infusion<br>2-6 mm static mixers<br>Lipid A Infusion<br>2-6 mm static mixers<br>1-10 mm static mixer<br>Salt Water Dilution Phase Infusion<br>2-10 mm static mixers | Aqueous Cleaning Phase Infusion<br>Lipid B Infusion<br>2-6 mm static mixers<br>Lipid A Infusion<br>1-6 mm static mixer<br>1-10 mm static mixer<br>Salt Water Dilution Phase Infusion<br>2-10 mm static mixers | Aqueous Cleaning Phase Infusion<br>Lipid A Infusion<br>2-6 mm static mixers<br>Lipid B Infusion<br>1-6 mm static mixer<br>1-10 mm static mixer<br>Salt Water Dilution Phase Infusion<br>2-10 mm static mixers | Aqueous Cleaning Phase Infusion<br>Lipid B Infusion<br>1-6 mm static mixer<br>Lipid A Infusion<br>2-6 mm static mixers<br>1-10 mm static mixer<br>Salt Water Dilution Phase Infusion<br>2-10 mm static mixers | Aqueous Cleaning Phase Infusion<br>Lipid A-Lipid B Comined Preblend Infusion<br>2-6 mm static mixers<br>1-10 mm static mixer<br>Salt Water Dilution Phase Infusion<br>2-10 mm static mixers |
| Petrolatum Deposition | 272 μg/cm2 | 272 μg/cm2 | 295 μg/cm2 | 301 μg/cm2 | 315 μg/cm2 | 349 μg/cm2 | 330 μg/cm2 | 70 μg/cm2 |

In the above table, the static mixers used were either six or ten mm in diameter, as indicated. Each static mixer unit consisted of six elements. The static mixers used were either one or two units of mixers for a total of six or twelve mixing elements. The static mixers used were SMX style static mixers from Sulzer.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any related patent or application identified in the Application Data Sheet accompanying this application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a personal care composition having enhancing deposition of a high viscosity benefit agent comprising:
    a) forming a structured cleansing phase combining from about 5% to about 20%, by weight of the personal care composition, of an anionic surfactant; and an amphoteric surfactant, a zwitterionic surfactant, or a combination thereof; a structuring system comprising from about 0.001% to about 5%, by weight of the personal care composition of acrylate/$C_{10}$-$C_{30}$ alkyl acrylate cross-polymer and from about 0.01% to about 5.0%, by weight of the personal care composition, of a non-associative polymer wherein the non-associative polymer is selected from the group consisting of polysaccharides, synthetic hydrocarbon polymers, and combinations thereof;
b) form a first benefit phase by introducing a high viscosity benefit agent into a tank and heating it to from about 50° C. to about 80° C.; wherein the high viscosity benefit agent is selected from the group consisting of petrolatum, microcrystalline wax/mineral oil blends, paraffin wax/mineral oil blends, wax/oil blends, glyceryl oleate, and combinations thereof;
c) form a second benefit phase by introducing a low viscosity benefit agent into a tank and heating it to from about 20° C. to about 60° C.; wherein the low viscosity benefit agent is selected from the group consisting of soy bean oil, sunflower seed oil, or a combination thereof;
d) combining the structured cleansing phase with the first and second benefit phases by injecting the first benefit phase into a mixing device selected from a static mixer, rotor-stator device, recirculation loop, and a mixing zone in a mix tank and mixing the first benefit phase with the structured cleansing phase; and then injecting the second benefit phase into a into the mixing device selected from a static mixer, rotor-stator device, recirculation loop, and a mixing zone in a mix tank and mixing the second benefit phase with the structured cleaning phase wherein the high viscosity benefit agent is in a first benefit phase comprising an average particle size of about 50 µm to about 500 µm; and the low viscosity benefit agent is in a second benefit phase comprising an average particle size of about 0.5 µm to about 10 µm.

2. The method of claim 1, wherein the personal care composition comprises from about 0.1% to about 20%, by the weight of the personal care composition, of the high viscosity benefit agent; and from about 0.1% to about 20%, by the weight of the personal care composition, of the low viscosity benefit agent.

* * * * *